(12) United States Patent
Hossainy et al.

(10) Patent No.: US 8,465,772 B2
(45) Date of Patent: *Jun. 18, 2013

(54) METHODS AND COMPOSITIONS FOR TREATING TISSUE USING SILK PROTEINS

(75) Inventors: Syed Hossainy, Fremont, CA (US); Michael Ngo, San Jose, CA (US); Mikael Trollsas, San Jose, CA (US); John Stankus, Campbell, CA (US); Gene Michal, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,324

(22) Filed: May 15, 2012

(65) Prior Publication Data

US 2012/0225040 A1 Sep. 6, 2012

Related U.S. Application Data

(62) Division of application No. 11/566,643, filed on Dec. 4, 2006, now Pat. No. 8,192,760.

(51) Int. Cl.
*A61K 35/28* (2006.01)
*A61K 47/48* (2006.01)
*A61K 47/42* (2006.01)
*A61K 9/00* (2006.01)
*A61K 9/08* (2006.01)
*C07K 17/08* (2006.01)
*A61F 2/00* (2006.01)
*C08L 89/00* (2006.01)

(52) U.S. Cl.
USPC .......... 424/484; 424/93.7; 424/577; 530/382; 530/812; 530/353; 523/113; 525/54.1

(58) Field of Classification Search
None
See application file for complete search history.

(56) References Cited

U.S. PATENT DOCUMENTS

| | | |
|---|---|---|
| 2,512,569 A | 6/1950 | Saffir |
| 3,144,868 A | 8/1964 | Jascalevich |
| 3,584,624 A | 6/1971 | de Ciutiis |
| 3,780,733 A | 12/1973 | Martinez-Manzor |
| 3,804,097 A | 4/1974 | Rudie |
| 3,890,976 A | 6/1975 | Bazell et al. |
| 4,141,973 A | 2/1979 | Balazs |
| 4,617,186 A | 10/1986 | Schafer et al. |
| 4,794,931 A | 1/1989 | Yock |
| 4,818,291 A | 4/1989 | Iwatsuki et al. |
| 4,842,590 A | 6/1989 | Tanabe et al. |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Slepian et al. |

(Continued)

FOREIGN PATENT DOCUMENTS

| | | |
|---|---|---|
| EP | 0331584 | 9/1989 |
| EP | 0861632 | 9/1998 |

(Continued)

OTHER PUBLICATIONS

Abbott Cardiovascular Systems, Office Action dated Apr. 6, 2009 for U.S. Appl. No. 11/447,340.

(Continued)

*Primary Examiner* — Marsha Tsay
(74) *Attorney, Agent, or Firm* — Blakely Sokoloff Taylor & Zafman LLP

(57) ABSTRACT

Compositions for forming a self-reinforcing composite biomatrix, methods of manufacture and use therefore are herein disclosed. Kits including delivery devices suitable for delivering the compositions are also disclosed. In some embodiments, the composition can include at least three components. In one embodiment, a first component can include a first functionalized polymer, a second component can include a second functionalized polymer and a third component can include silk protein or constituents thereof. In some embodiments, the composition can include at least one cell type and/or at least one growth factor. In some embodiments, the composition can include a biologic encapsulated, suspended, disposed within or loaded into a biodegradable carrier. In some embodiments, the composition(s) of the present invention can be delivered by a dual lumen injection device to a treatment area in situ, in vivo, as well as ex vivo applications.

24 Claims, 6 Drawing Sheets

U.S. PATENT DOCUMENTS

| | | | |
|---|---|---|---|
| 5,580,714 A | 12/1996 | Polovina | |
| 5,580,856 A | 12/1996 | Prestrelski et al. | |
| 5,588,432 A | 12/1996 | Crowley | |
| 5,621,610 A | 4/1997 | Moore et al. | |
| 5,631,011 A * | 5/1997 | Wadstrom | 424/400 |
| 5,642,234 A | 6/1997 | Altman et al. | |
| 5,655,548 A | 8/1997 | Nelson et al. | |
| 5,667,778 A | 9/1997 | Atala | |
| 5,669,883 A | 9/1997 | Scarfone et al. | |
| 5,672,153 A | 9/1997 | Lax et al. | |
| 5,676,151 A | 10/1997 | Yock | |
| 5,693,029 A | 12/1997 | Leonhardt | |
| 5,722,403 A | 3/1998 | McGee et al. | |
| 5,725,551 A | 3/1998 | Myers et al. | |
| 5,730,732 A | 3/1998 | Sardelis et al. | |
| 5,740,808 A | 4/1998 | Panescu et al. | |
| 5,749,915 A | 5/1998 | Slepian | |
| 5,785,689 A | 7/1998 | De Toledo et al. | |
| 5,795,331 A | 8/1998 | Cragg et al. | |
| 5,810,885 A | 9/1998 | Zinger | |
| 5,811,533 A | 9/1998 | Gold et al. | |
| 5,827,313 A | 10/1998 | Ream | |
| 5,843,156 A | 12/1998 | Slepian et al. | |
| 5,874,500 A | 2/1999 | Rhee et al. | |
| 5,879,713 A | 3/1999 | Roth et al. | |
| 5,900,433 A | 5/1999 | Igo et al. | |
| 5,906,934 A | 5/1999 | Grande et al. | |
| 5,919,449 A | 7/1999 | Dinsmore | |
| 5,935,160 A | 8/1999 | Auricchio et al. | |
| 5,939,323 A | 8/1999 | Valentini et al. | |
| 5,941,868 A | 8/1999 | Kaplan et al. | |
| 5,957,941 A | 9/1999 | Ream | |
| 5,968,064 A | 10/1999 | Selmon | |
| 5,979,449 A | 11/1999 | Steer | |
| 5,980,887 A | 11/1999 | Isner et al. | |
| 5,981,568 A | 11/1999 | Kunz et al. | |
| 5,984,908 A | 11/1999 | Davis et al. | |
| 5,997,536 A | 12/1999 | Osswald et al. | |
| 6,022,540 A | 2/2000 | Bruder et al. | |
| 6,045,565 A | 4/2000 | Ellis et al. | |
| 6,050,949 A | 4/2000 | White et al. | |
| 6,051,071 A | 4/2000 | Charvet et al. | |
| 6,051,648 A | 4/2000 | Rhee et al. | |
| 6,056,744 A | 5/2000 | Edwards | |
| 6,058,329 A | 5/2000 | Salo et al. | |
| 6,060,053 A | 5/2000 | Atala | |
| 6,071,305 A | 6/2000 | Brown et al. | |
| 6,086,582 A | 7/2000 | Altman et al. | |
| 6,093,177 A | 7/2000 | Javier, Jr. et al. | |
| 6,099,563 A | 8/2000 | Zhong | |
| 6,099,864 A | 8/2000 | Morrison et al. | |
| 6,102,887 A | 8/2000 | Altman | |
| 6,102,904 A | 8/2000 | Vigil et al. | |
| 6,102,926 A | 8/2000 | Tartaglia et al. | |
| 6,120,520 A | 9/2000 | Saadat et al. | |
| 6,120,904 A | 9/2000 | Hostettler et al. | |
| 6,127,448 A | 10/2000 | Domb | |
| 6,133,231 A | 10/2000 | Ferrara et al. | |
| 6,134,003 A | 10/2000 | Tearney et al. | |
| 6,146,373 A | 11/2000 | Cragg et al. | |
| 6,151,525 A | 11/2000 | Soykan | |
| 6,152,141 A | 11/2000 | Stevens et al. | |
| 6,153,428 A | 11/2000 | Gustafsson et al. | |
| 6,159,443 A | 12/2000 | Hallahan et al. | |
| 6,162,202 A | 12/2000 | Sicurelli et al. | |
| 6,175,669 B1 | 1/2001 | Colston et al. | |
| 6,177,407 B1 | 1/2001 | Rodgers et al. | |
| 6,179,809 B1 | 1/2001 | Khairkhahan et al. | |
| 6,183,432 B1 | 2/2001 | Milo | |
| 6,183,444 B1 | 2/2001 | Glines et al. | |
| 6,187,330 B1 | 2/2001 | Wang et al. | |
| 6,190,353 B1 | 2/2001 | Makower et al. | |
| 6,191,144 B1 | 2/2001 | Isner | |
| 6,192,271 B1 | 2/2001 | Hayman | |
| 6,193,763 B1 | 2/2001 | Mackin | |
| 6,197,324 B1 | 3/2001 | Crittenden | |
| 6,201,608 B1 | 3/2001 | Mandella et al. | |
| 6,206,893 B1 | 3/2001 | Klein et al. | |
| 6,206,914 B1 | 3/2001 | Soykan et al. | |
| 6,207,180 B1 | 3/2001 | Ottoboni et al. | |
| 6,210,392 B1 | 4/2001 | Vigil et al. | |
| 6,217,527 B1 | 4/2001 | Selmon et al. | |
| 6,217,554 B1 | 4/2001 | Green | |
| 6,221,049 B1 | 4/2001 | Selmon et al. | |
| 6,231,546 B1 | 5/2001 | Milo et al. | |
| 6,235,000 B1 | 5/2001 | Milo et al. | |
| 6,241,710 B1 | 6/2001 | Van Tassel et al. | |
| 6,251,104 B1 | 6/2001 | Kesten et al. | |
| 6,283,947 B1 | 9/2001 | Mirzaee | |
| 6,287,285 B1 | 9/2001 | Michal et al. | |
| 6,290,729 B1 | 9/2001 | Slepian et al. | |
| 6,296,602 B1 | 10/2001 | Headley | |
| 6,299,604 B1 | 10/2001 | Ragheb et al. | |
| 6,309,370 B1 | 10/2001 | Haim et al. | |
| 6,312,725 B1 | 11/2001 | Wallace et al. | |
| 6,315,994 B2 | 11/2001 | Usala et al. | |
| 6,323,278 B2 | 11/2001 | Rhee et al. | |
| RE37,463 E | 12/2001 | Altman | |
| 6,328,229 B1 | 12/2001 | Duronio et al. | |
| 6,331,309 B1 | 12/2001 | Jennings, Jr. et al. | |
| 6,333,194 B1 | 12/2001 | Levy et al. | |
| 6,334,872 B1 | 1/2002 | Termin et al. | |
| 6,338,717 B1 | 1/2002 | Ouchi | |
| 6,346,098 B1 | 2/2002 | Yock et al. | |
| 6,346,099 B1 | 2/2002 | Altman | |
| 6,346,515 B1 | 2/2002 | Pitaru et al. | |
| 6,358,247 B1 | 3/2002 | Altman et al. | |
| 6,358,258 B1 | 3/2002 | Arcia et al. | |
| 6,360,129 B1 | 3/2002 | Ley et al. | |
| 6,368,285 B1 | 4/2002 | Osadchy et al. | |
| 6,371,935 B1 | 4/2002 | Macoviak et al. | |
| 6,371,992 B1 | 4/2002 | Tanagho et al. | |
| 6,379,379 B1 | 4/2002 | Wang | |
| 6,385,476 B1 | 5/2002 | Osadchy et al. | |
| 6,391,052 B2 | 5/2002 | Buirge et al. | |
| 6,395,023 B1 | 5/2002 | Summers | |
| 6,409,716 B1 | 6/2002 | Sahatjian et al. | |
| 6,416,510 B1 | 7/2002 | Altman et al. | |
| 6,425,887 B1 | 7/2002 | McGuckin et al. | |
| 6,432,119 B1 | 8/2002 | Saadat | |
| 6,436,135 B1 | 8/2002 | Goldfarb | |
| 6,440,947 B1 | 8/2002 | Barron et al. | |
| 6,443,941 B1 | 9/2002 | Slepian et al. | |
| 6,443,949 B2 | 9/2002 | Altman | |
| 6,447,504 B1 | 9/2002 | Ben-Haim et al. | |
| 6,458,095 B1 | 10/2002 | Wirt et al. | |
| 6,458,098 B1 | 10/2002 | Kanesaka | |
| 6,464,862 B2 | 10/2002 | Bennett | |
| 6,465,001 B1 | 10/2002 | Hubbell et al. | |
| 6,478,775 B1 | 11/2002 | Galt et al. | |
| 6,478,776 B1 | 11/2002 | Rosenman et al. | |
| 6,482,231 B1 | 11/2002 | Abatangelo et al. | |
| 6,485,481 B1 | 11/2002 | Pfeiffer | |
| 6,494,862 B1 | 12/2002 | Ray et al. | |
| 6,514,217 B1 | 2/2003 | Selmon et al. | |
| 6,544,230 B1 | 4/2003 | Flaherty et al. | |
| 6,548,081 B2 | 4/2003 | Sadozai et al. | |
| 6,554,801 B1 | 4/2003 | Steward et al. | |
| 6,599,267 B1 | 7/2003 | Ray et al. | |
| 6,602,241 B2 | 8/2003 | Makower et al. | |
| 6,616,869 B2 | 9/2003 | Mathiowitz et al. | |
| 6,624,245 B2 | 9/2003 | Wallace et al. | |
| 6,628,988 B2 | 9/2003 | Kramer et al. | |
| 6,629,947 B1 | 10/2003 | Sahatjian et al. | |
| 6,632,457 B1 | 10/2003 | Sawhney | |
| 6,635,267 B1 | 10/2003 | Miyoshi et al. | |
| 6,660,034 B1 | 12/2003 | Mandrusov et al. | |
| 6,682,730 B2 | 1/2004 | Mickel et al. | |
| 6,689,608 B1 | 2/2004 | Mikos et al. | |
| 6,692,466 B1 | 2/2004 | Chow et al. | |
| 6,702,744 B2 | 3/2004 | Mandrusov et al. | |
| 6,706,034 B1 | 3/2004 | Bhat | |
| 6,726,677 B1 | 4/2004 | Flaherty et al. | |
| 6,737,072 B1 | 5/2004 | Angele et al. | |
| 6,748,258 B1 | 6/2004 | Mueller et al. | |
| 6,749,617 B1 | 6/2004 | Palasis et al. | |
| 6,759,431 B2 | 7/2004 | Hunter et al. | |

| | | |
|---|---|---|
| 6,761,887 B1 | 7/2004 | Kavalkovich et al. |
| 6,777,231 B1 | 8/2004 | Katz et al. |
| 6,790,455 B2 | 9/2004 | Chu et al. |
| 6,824,791 B2 | 11/2004 | Mathiowitz et al. |
| 6,858,229 B1 | 2/2005 | Hubbell et al. |
| 6,916,488 B1 | 7/2005 | Meier et al. |
| 6,916,648 B2 | 7/2005 | Goddard et al. |
| 6,926,692 B2 | 8/2005 | Katoh et al. |
| 6,992,172 B1 | 1/2006 | Chang et al. |
| 7,008,411 B1 | 3/2006 | Mandrusov et al. |
| 7,035,092 B2 | 4/2006 | Hillman et al. |
| 7,112,587 B2 | 9/2006 | Timmer et al. |
| 7,129,210 B2 | 10/2006 | Lowinger et al. |
| 7,169,127 B2 | 1/2007 | Epstein et al. |
| 7,270,654 B2 | 9/2007 | Griego et al. |
| 7,273,469 B1 | 9/2007 | Chan et al. |
| 7,361,360 B2 | 4/2008 | Kitabwalla et al. |
| 7,374,774 B2 | 5/2008 | Bowlin et al. |
| 7,393,339 B2 | 7/2008 | Zawacki et al. |
| 7,438,692 B2 | 10/2008 | Tsonton et al. |
| 7,615,373 B2 | 11/2009 | Simpson et al. |
| 7,732,190 B2 | 6/2010 | Michal et al. |
| 7,815,590 B2 | 10/2010 | Cooper |
| 8,192,760 B2 | 6/2012 | Hossainy et al. |
| 2001/0023349 A1 | 9/2001 | Van Tassel et al. |
| 2001/0055615 A1 | 12/2001 | Wallace et al. |
| 2002/0013408 A1 | 1/2002 | Rhee et al. |
| 2002/0042473 A1 | 4/2002 | Trollsas et al. |
| 2002/0072706 A1 | 6/2002 | Hiblar et al. |
| 2002/0076441 A1 | 6/2002 | Shih et al. |
| 2002/0090725 A1 | 7/2002 | Simpson et al. |
| 2002/0102272 A1 | 8/2002 | Rosenthal et al. |
| 2002/0124855 A1 | 9/2002 | Chachques |
| 2002/0131974 A1 | 9/2002 | Segal |
| 2002/0142458 A1 | 10/2002 | Williams et al. |
| 2002/0146557 A1 | 10/2002 | Claude et al. |
| 2002/0151867 A1 | 10/2002 | McGuckin et al. |
| 2002/0169420 A1 | 11/2002 | Galt et al. |
| 2002/0188170 A1 | 12/2002 | Santamore et al. |
| 2003/0023202 A1 | 1/2003 | Nielson |
| 2003/0040712 A1 | 2/2003 | Ray et al. |
| 2003/0050597 A1 | 3/2003 | Dodge et al. |
| 2003/0078671 A1 | 4/2003 | Lesniak et al. |
| 2003/0105493 A1 | 6/2003 | Salo |
| 2003/0175410 A1 | 9/2003 | Campbell et al. |
| 2004/0002650 A1 | 1/2004 | Mandrusov et al. |
| 2004/0181206 A1 | 9/2004 | Chiu et al. |
| 2004/0185084 A1 | 9/2004 | Rhee et al. |
| 2004/0208845 A1 | 10/2004 | Michal et al. |
| 2004/0213756 A1 | 10/2004 | Michal et al. |
| 2004/0229856 A1 | 11/2004 | Chandrasekar et al. |
| 2005/0015048 A1 | 1/2005 | Chiu et al. |
| 2005/0031874 A1 | 2/2005 | Michal et al. |
| 2005/0042254 A1 | 2/2005 | Freyman et al. |
| 2005/0064038 A1 | 3/2005 | Dinh et al. |
| 2005/0065281 A1 | 3/2005 | Lutolf et al. |
| 2005/0070844 A1 | 3/2005 | Chow et al. |
| 2005/0186240 A1 | 8/2005 | Ringeisen et al. |
| 2005/0281883 A1 | 12/2005 | Daniloff et al. |
| 2006/0149392 A1 | 7/2006 | Hsieh et al. |
| 2006/0233850 A1 | 10/2006 | Michal |
| 2007/0270948 A1 | 11/2007 | Wuh |
| 2008/0025943 A1 | 1/2008 | Michal et al. |
| 2012/0225040 A1 | 9/2012 | Hossainy et al. |
| 2012/0225041 A1 | 9/2012 | Hossainy et al. |

FOREIGN PATENT DOCUMENTS

| | | |
|---|---|---|
| EP | 0938871 | 9/1999 |
| EP | 1214077 | 1/2004 |
| FR | 2715855 | 8/1995 |
| GB | 2194144 | 3/1988 |
| JP | 61205446 | 9/1986 |
| JP | 10236984 | 9/1998 |
| JP | 2000502380 | 2/2000 |
| JP | 2000262525 | 9/2000 |
| JP | 2003062089 | 3/2003 |
| WO | WO-9210142 | 6/1992 |
| WO | WO-9830207 | 7/1998 |
| WO | WO-9854301 | 12/1998 |
| WO | WO-9953943 | 10/1999 |
| WO | WO-0016818 | 3/2000 |
| WO | WO-0054661 | 9/2000 |
| WO | WO-0071196 | 11/2000 |
| WO | WO-0124775 | 4/2001 |
| WO | WO-0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |
| WO | WO-02072166 | 9/2002 |
| WO | WO-02087623 | 11/2002 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-04000915 | 12/2003 |
| WO | WO-2004050013 | 6/2004 |
| WO | WO-2004058305 | 7/2004 |
| WO | WO-2004066829 | 8/2004 |
| WO | WO-2004091592 | 10/2004 |
| WO | WO-2004098669 | 11/2004 |
| WO | WO-2005061019 | 7/2005 |
| WO | WO-2005067890 | 7/2005 |
| WO | WO-2006027549 | 3/2006 |
| WO | WO-2006039704 | 4/2006 |
| WO | WO-2006113407 | 10/2006 |
| WO | WO-2007048831 | 3/2007 |
| WO | WO-2007145909 | 12/2007 |

OTHER PUBLICATIONS

Abbott Cardiovascular Systems, Office Action dated Mar. 30, 2009 for U.S. Appl. No. 10/792,960.

Abbott Cardiovascular Systems, Office Action dated Apr. 13, 2009 for U.S. Appl. No. 11/566,643.

Abbott Cardiovascular Systems, Product Information Sheet for HEALON (R), from Abbott Medical Optics, (2005), 1 page.

Abbott Cardiovascular Systems, website for HEALON (R) OVD, copyright 2010, accessed Dec. 15, 2010, URL: <http://abbottmedicaloptics.com/products/cataract/ovds/healon-viscoelastic>, (2010), 2 pages.

Abbott Cardiovascular Systems, Non-final Office Action mailed Dec. 17, 2010 for U.S. Appl. No. 11/933,922, 23 pages.

Abbott Cardiovascular Systems, Non-final Office Action mailed Dec. 8, 2010 for U.S. Appl. No. 11/566,643, 17 pages.

Abbott Cardiovascular Systems, Non final office action dated Aug. 13, 2010 for U.S. Appl. No. 11/447,340.

Abbott Cardiovascular Systems, Non-Final Office Action dated Jun. 4, 2010 for U.S. Appl. No. 10/781,984.

Abbott Cardiovascular Systems, Final Office Action dated Jan. 29, 2010 for U.S. Appl. No. 10/792,960.

Abbott Cardiovascular Systems, Non final office action dated Feb. 5, 2010 for U.S. Appl. No. 11/447,340.

Abbott Cardiovascular Systems, Examination Report dated Jan. 13, 2010 for EP Application No. 07795729.8.

Abbott Cardiovascular Systems, Final office action dated Nov. 12, 2009 for U.S. Appl. No. 12/013,286.

Abbott Cardiovascular Systems, International search report and written opinion dated Jun. 18, 2009 for PCT/US2008/051505.

Abbott Cardiovascular Systems, Non-final Office Action mailed Nov. 24, 2010 for U.S. Appl. No. 12/013,286, 11 pages.

Abbott Cardiovascular Systems, Final Office Action mailed Nov. 22, 2010 for U.S. Appl. No. 10/781,984, 13 pages.

Abbott Cardiovascular Systems, Final office action dated Nov. 25, 2009 for U.S. Appl. No. 11/566,643.

Abbott Cardiovascular Systems, Non final office action mailed Nov. 8, 2011 for U.S. Appl. No. 10/792,960.

Abbott Cardiovascular Systems, Final office action mailed Sep. 20, 2011 for U.S. Appl. No. 11/938,752.

Abbott Cardiovascular Systems, Final office action mailed Jun. 28, 2011 for U.S. Appl. No. 10/792,960.

Abbott Cardiovascular Systems, Non final office action mailed Jul. 6, 2011 for U.S. Appl. No. 10/781,984.

Abbott Cardiovascular Systems, Final Office Action dated Jun. 11, 2010 for U.S. Appl. No. 11/561,328.
Abbott Cardiovascular Systems, Non final office action dated Apr. 29, 2010 for U.S. Appl. No. 10/792,960.
Abbott Cardiovascular Systems, Final office action mailed Sep. 27, 2010 for U.S. Appl. No. 10/792,960.
Abbott Cardiovascular Systems, Examination Report dated Feb. 5, 2010 for EP 07810637.4.
Abbott Cardiovascular Systems, Non final office action dated Dec. 9, 2009 for U.S. Appl. No. 10/781,984.
Abbott Cardiovascular Systems, Non final office action dated Jul. 9, 2009 for U.S. Appl. No. 11/561,328.
Abbott Cardiovascular Systems, Non-Final Office action dated Mar. 13, 2009 for U.S. Appl. No. 10/414,602.
Abbott Cardiovascular Systems, Office Ation dated Apr. 29, 2009 for U.S. Appl. No. 12/013,286.
Abbott Cardiovascular Systems, Office Action mailed Jan. 17, 2012 for European Patent Application 08727952.7, 6 pages.
Abbott Cardiovascular Systems, Final Office Action mailed Jan. 5, 2012 for U.S. Appl. No. 11/361,920, 13 pages.
Abbott Cardiovascular Systems, Final Office Action mailed Oct. 21, 2011 for U.S. Appl. No. 10/781,984, 10 pages.
Abbott Cardiovascular Systems, Non-Final Office Action mailed Aug. 31, 2011 for U.S. Appl. No. 11/110,223, 11 pages.
Abbott Cardiovascular Systems, Final office action mailed Jul. 18, 2011 for U.S. Appl. No. 11/566,643.
Abbott Cardiovascular Systems, Non final office action mailed Jun. 7, 2011 for U.S. Appl. No. 11/447,340.
Abbott Cardiovascular Systems, Final Office Action mailed Apr. 15, 2011 for U.S. Appl. No. 10/414,602.
Abbott Cardiovascular Systems, Japanese Office Action dated Dec. 8, 2010 for Jasanese Patent App No. 2006-509975., 6 pages.
Abbott Cardiovascular Systems, Final office action dated Apr. 22, 2010 for U.S. Appl. No. 10/414,602.
Abbott Cardiovascular Systems, Non final office action dated Apr. 14, 2010 for U.S. Appl. No. 12/016,180.
Abbott Cardiovascular Systems, International Preliminary Report on Patentability dated Jul. 30, 2009 for PCT/US2008/051505.
Abbott Cardiovascular Systems, Non final office action mailed Feb. 8, 2011 for U.S. Appl No. 10/792,960.
Abbott Cardiovascular Systems, Non-final Office action mailed Dec. 10, 2010 for U.S. Appl No. 11/938,752, 32 pages.
Abbott Cardiovascular Systems, Final office action mailed Sep. 27, 2010 for U.S. Appl No. 12/016,180.
Abbott Cardiovascular Systems, Examination Report dated Jan. 15, 2010 for EP 08727952.7.
Abbott Cardiovascular Systems, Office action dated May 12, 2009 for U.S. Appl No. 11/496,824.
Abbott Cardiovascular Systems Inc., PCT International Preliminary Report on Patentability and Written Opinion dated Dec. 24, 2008 for PCT/US2007/013181., P4437X2PCT.
Abbott Cardiovascular Systems Inc., PCT Search Report and Written Opinion dated Aug. 26, 2008 for PCT/US2007/016433.
Abbott Cardiovascular Systems Inc., PCT Search Report and Written Opinion dated Jul. 31, 2008 for PCT/US2007/024158.
Abbott Cardiovascular Systems in, "PCT International Search Report and Written Opinion mailed Feb. 10, 2009", PCT/US2007/023419.
Abbott Cardiovascular Systems Inc., "PCT Search Report dated Feb. 12, 2008", PCT Appln No. PCT/US2007/013181, 17.
Abbott Cardiovascular Systems Inc., "PCT Search Report dated Jan. 31, 2007", PCT Appln No. PCT/US2006/014021, 11.
Abbott Cardiovascular Systems Inc., "PCT Search Report dated Mar. 27, 2008", PCT Appln No. PCT/US2007/003614, 18.
Advanced Cardiovascular Systems, Extended EP Search Report dated May 20, 2011 for EP Application No. 10186197.9.
Advanced Cardiovascular Systems, Extended European search report dated Apr. 21, 2011 for EP Application No. 10186186.2.
Advanced Cardiovascular Systems, Inc., et al., "PCT International Preliminary Report on Patentability dated Jun. 19, 2007", PCT Appln. No. PCT/US2005/045627.
Advanced Cardiovascular Systems, Inc., "PCT International Preliminary Report on Patentability dated Nov. 3, 2005", CT Appln. No. PCT/US2004/011356, 6 pages.
Advanced Cardiovascular Systems, Inc., "PCT International Search Report and Written Opinion mailed Oct. 13, 2006", PCT Appln No. PCT/US2005/045627.
Advanced Cardiovascular Systems, Inc., "PCT International Search Report dated Feb. 9, 2004", PCT Appln. No. PCT/US03/30464, 5 pages.
Advanced Cardiovascular Systems, Inc., "PCT International Search Report dated Jan. 28, 2004", PCT Appln. No. PCT/US03/18360, 7 pages.
Advanced Cardiovascular Systems, Inc. Appln No. PCT/US03/18360, 3 pages.
Advanced Cardiovascular Systems, Inc., "PCT Search Report and Written Opinion dated Nov. 24, 2004", PCT Appln. No. PCT/US2004/011356, 12 pages.
Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29 (8), (Apr. 1997) pp. 2233-2244.
Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at www.ncbi.nlm.nih.gov/entrez/query.fcgi?cmd=Retrieve&db=PubMed, (Nov. 1997), 229-234.
Anderson, James M., et al., "Biodegradation and biocompatibility of PLA and PLGA microspheres", Advanced Drug Delivery Reviews 28, (1997), 5-24.
Assmus, B., et al., "Transplantation of Progenitor Cells and Regeneration Enhancement in Acute Myocardial Infarction (TOPCARE-AMI)", Clinical Investigation and Reports, Circulation, 106, (2002), 3009-3017.
Baxter Healthcare Corporation, "FloSeal Matrix Hemostatic Sealant", fusionmed.com/docs/surgeon/default.asp, (2002), pp. 1-2.
Berger, et al., "Poly-L-cysteine", J. Am. Chem. Soc., 78(17), (Sep. 5, 1956), pp. 4483-4488.
Bernatowicz, M., et al., "Preparation of Boc-[S-(3-nitro-2-pyridinesulfenyl)]- cysteine and its use for Unsymmetrical Disulfide Bond Formation", Int. J. Peptide Protein Res. 28(2), (Aug. 1996), pp. 107-112.
Boland, E. D., "Electrospinning Collagen and Elastin: Preliminary Vascular Tissue Engineering", Frontiers in Bioscience, vol. 9, (May 1, 2004), pp. 1422-1432.
Brust, G., "Polyimides", Department of Polymer Science; The University of Southern Mississippi, pslc.usm.edu/macrog/imide.htm, (2005), pp. 1-4.
Buschmann, I, et al., "Arteriogenesis versus angiogenesis: Two mechanisms of vessel growth", News Physiol. Sci., vol. 14, (Jun. 1999), 121-125.
Canderm Pharma, "Technical Dossier: Artecoll", downloaded from the Internet on Oct. 22, 2002 from: http://www.canderm.com/artecoll/tech.html, pp. 1-3.
Capan, Y., et al., "Preparation and Characterization of Poly(D,L-lactide-co-glycolide) Microspheres for Controlled Release of Human Growth Hormone", AAPS PharmSciTech., 4(2 Article 28, (2003), 1-10.
Caplan, Michael J., et al., "Dependence on pH of polarized sorting of selected proteins", Nature, vol. 29, (Oct. 15, 1987), 630.
Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.
Chandy, et al., "The development of porous alginate/elastin/PEG composite matrix for cardiovascular engineering", Journal of Biomaterials Applications, vol. 17, (Apr. 2003), 287-301.
Choi, Young Seon, et al., "Study on gelatin-containing artificial skin: I. Preparation and characteristics of novel gelatin-alginate sponge", Biomaterials, vol. 20, (1999), 409-417.
Chung, Y. , et al., "Sol-gel transition temperature of PLGA-g-PEG aqueous solutions", iomacromolecules, vol. 3, No. 3, (May 2002), 511-516.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.

Creemers, E., et al., "Matrix Metalloproteinase Inhibition After Myocardial Infarction: A New Approach to Prevent Heart Failure?", Circ. Res., vol. 89, (2001), pp. 201-210.

Crivello, et al., "Synthesis and Photoinitiated Cationic Polymerization of Monomers with the Silsesquioxane Core", J Polym Science: Part A: Polymer Chemistry 35, (1997), 407-425.

Davis, M. E., et al., "Injectable Self-Assembling Peptide Nanofibers Create Intramyocardial Microenvironments for Endothelial Cells", Circulation, 111, (Feb. 2005), pp. 442-450.

De Rosa, et al., "Biodegradable Microparticles for the Controlled Delivery of Oligonucleotides", International Journal of Pharmaceutics, 242, (Aug. 21, 2002), pp. 225-228.

Desai, M., et al., "Polymer bound EDC (P-EDC): A convenient reagent for formation of an amide bond", Tetrahedron Letters, 34(48), Abstract downloaded from the Internet at sciencedirect.com, (Nov. 1993), 7685-7688.

Dinbergs, et al., "Cellular response to transforming growth factor-β1 and basic fibroblast growth factor depends on release kinetics and extracellular matrix interactions", The Journal of Biological Chemistry, vol. 271, No. 47, (Nov. 1996), 29822-29829.

Dong, Zhanfeng, et al., "Alginate/gelatin blend films and their properties for drug controlled release", Journal of Membrane Science, vol. 280, (2006), 37-44.

Edelman, "Controlled and modulated release of basic fibroblast growth factor", Biomaterials, vol. 12, (Sep. 1999), 619-626.

Elbert, D. L., et al., "Protein delivery from materials formed by self-selective conjugate addition reactions", Journal of Controlled Release, 76, (2001), 11-25.

Etzion, S., et al., "Influence of Embryonic Cardiomyocyte Transplanation on the Progression of Heart Failure in a Rat Model of Extensive Myocardial Infarction", J. Mol. Cell Cardiol., 33, (May 2001), pp. 1321-1330.

Ferrara, N., "Role of Vascular Endothelial Growth Factor in the Regulation of Angiogenesis", Kidney International, 56(3), Abstract downloaded from the Internet at nature.com/ki/journal/v56/n3/abs/4490967a.html, (1999), 794-814.

Friedman, Paul M., et al., "Safety Data of Injectable Nonanimal Stabilized Hyaluronic Acid Gel for Soft Tissue Augmentation", Dermatologic Surgery, vol. 28, (2002), pp. 491-494.

Fuchs, S.. et al., "Catheter-Based Autologous Bone Marrow Myocardial Injection in No-Option Patients with Advanced Coronary Artery Disease", J. Am. Coll. Cardiol., 41(10), (2003), pp. 1721-1724.

Fukumoto, S., et al., "Protein Kinase C δ Inhibits the Proliferation of Vascular Smooth Muscle Cells by Suppressing G1 Cyclin Expression", The Journal of Biological Chemistry, 272(21), (May 1997), pp. 13816-13822.

Giordano, F., et al., "Angiogenesis: The Role of the Microenvironment in Flipping the Switch", Current Opinion in Genetics and Development, 11, (2001), pp. 35-40.

Gossler, et al., "Transgenesis by means of blastocyst-derived embryonic stem cell lines", Proc. Natl. Acad. Sci. USA, 83, (Dec. 1986), pp. 9065-9069.

Grafe, T. H., "Nanofiber Webs from Electrospinning", Presented at the Nonwovens in Filtration—Fifth International Conference,, Stuttgart, Germany, (Mar. 2003), pp. 15.

Gref, R., et al., "Biodegradable Long-Circulating Polymeric Nanospheres", Science, 263(5153), Abstract downloaded from the Internet at: http://www.sciencemag.org/cgi/content/abstract/263/5153/1600, 1 page, (Mar. 1994).

Grund, F., et al., "Microembolization in Pigs: Effects on Coronary Blood Flow and Myocardial Ischemic Tolerance", Am. J. Physiol., 277 (Heart Circ. Physiol. 46), (1999), pp. H533-H542.

Gupta, et al., "Changes in Passive Mechanical Stiffness of Myocardial Tissue with Aneurysm Formation", Circulation, 89(5), (May 1994), pp. 2315-2326.

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.

Hao, X , et al., "Angiogenic effects of sequential release of VEGF-A165 and PDGF-BB with alginate hydrogels after myocardial infarction", Cardiovascular Research, 75, (2007), 178-185.

Hashimoto, T., et al., "Development of Alginate Wound Dressings Linked with Hybrid Peptides Derived from Laminin and Elastin", Biomaterials, 25, (2004), pp. 1407-1414.

Haugland, et al., "Dialkylcarbocyanine and Dialkylaminostryryl of Probes", Handbook of Fluorescent Probes and Research Products, Molecular Probes, Inc., (2002), 530-534.

Haugland, et al., "Membrane-permeant reactive tracers", Handbook of Fluorescent Probes and Research Products, Molecular Probes, Inc., (2002), 458-553.

Haynesworth, Stephen E., et al., "Platelet Effects on Human Mesenchymal Stem Cells", Abstract, presented at Orthopaedic Research Society 48th Annual Meeting, Dallas, TX, (Feb. 10-13, 2010), 2 pages.

Heeschen, C., et al., "Nicotine Stimulates Tumor Angiogenesis", American College of Cardiology, 37(2) Supplement A,, Abstract downloaded from the Internet at: http://24.132.160.238/ciw-01acc/abstract_search_author.cfm?SearchName=Heeschen, 1 page, (Feb. 2001), pp. 1A-648A.

Helisch, A, et al., "Angiogenesis and arteriogenesis", NEUE Diagnostische Und Therap. Verfahren, Z Kardiol 89, (2000), 239-244.

Hendel, R. C., et al., "Effect of Intracoronary Recombinant Human Vascular Endothelial Growth Factor on Myocardial Perfusion: Evidence for a Dose-Dependent Effect", Circulation, 101, (2000), pp. 118-121.

Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at www.diabetes.diabetesjournals.org/cgi/content/abstract/44/8/936, (1995), pp. 936-946.

Hoffman, "Hydrogels for Biomedical Applications", Advanced Drug Delivery Reviews, vol. 43, (2002), pp. 3-12.

Holland, N. B., et al., "Biomimetic Engineering of Non-Adhesive glycocalyx-like Surfaces Using Oligosaccharide Surfactant Polymers", Nature, 392, Abstract downloaded from the Internet at www.nature.com, (Apr. 1998), pp. 799-801.

Horan, R.L., et al., "In Vitro Degradation of Silk Fibroin", Biomaterials, vol. 26, (2004), 3385-3393.

Hovinen, J., et al., "Synthesis of 3'-functionalized oligonucleotides on a single solid support", Tetrahedron Letters, 34(50), Abstract downloaded from the Internet at www.sciencedirect.com, (Dec. 1993), pp. 8169-8172.

Huang, K., et al., "Synthesis and Characterization of Self-Assembling Block Copolymers Containing Bioadhesive End Groups", Biomacromolecules, 3(2), (2002), pp. 397-406.

Hutcheson, K. , et al., "Comparison of Benefits on Myocardial Performance of Cellular Cardiomyoplasty with Skeletal Myoblasts and Fibroblasts", Cell Transplantation, 9(3), (2000), pp. 359-368.

Huynh, T. V., et al., "Constructing and Screening cDNA Libraries in λgt10 and λgt11", Chapter 2 in DNA CLoning, vol. 1: A Practical Approach, ed. by D.M. Glover, (1985), pp. 49-78.

Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, (Jul. 1990), pp. 80-86.

Iskandrian, A. S., at al., "Nuclear Cardiac Imaging: Principles and Applications", second edition, F.A. Davis Co., Philadelphia, cover page, title page and TOC, (1996), 5 pages total.

Isner, J. M., "Vascular Endothelial Growth Factor: Gene Therapy and Therapeutic Angiogenesis", Am. J. Cardiol., 82(10A), (Nov. 19, 1998), pp. 63S-64S.

Ito, Wulf D., et al., "Monocyte chemotactic protein-1 increases collateral and peripheral conductance after femoral artery occlusion", Max-Planck-Institute for Physiological and Clinical Research, Bad Nauheim, Germany, (Feb. 21, 1997), 829-837.

Johnson, et al., "The stabilization and encapsulation of human growth hormone nto biodegradable microspheres", Pharmaceutical Research, vol. 14, No. 6, (1997), 730-735.

Jonasson, P., et al., "Denatured states of human carbonic anhydrase II: an NMR study of hydrogen/deuterium exchange at tryptophan-indole-Hn sites", FEBS Letters, 445, (1999), pp. 361-365.

Kalltorp, Mia, et al., "Inflammatory cell recruitment, distribution, and chemiluminescence response at IgG precoated- and thiol functionalized gold surfaces", Swedish Biomaterials Consortium, Swedish Foundation for Strategic Research, (Apr. 9, 1999), 251-259.

Kaplan, D.L., et al., "Spiderless Spider Webs", Nature Biotechnology, vol. 20, (2002), 239-240.

Kawai, et al., "Accelerated tissue regeneration through incorporation of basic fibroblast growth factor-impregnated gelatin microspheres into artificial dermis", Biomaterials, 21(5), (Mar. 2000), 489-499.

Kawasuji, M., et al., "Therapeutic Angiogenesis with Intramyocardial Administration of Basic Fibroblast Growth Factor", Ann Thorac Surg, 69, Abstract downloaded from the Internet at www.ats.ctsnetjournals.org/cgi/content/abstract/69/4/1155, (2000), pp. 1155-1161.

Kelley, et al., "Restraining Infarct Expansion Preserves Left Ventricular Geometry and Function After Acute Anteroapical Infarction", Circulation, 99, (1999), pp. 135-142.

Kelly, E. B., "Advances in Mammalian and Stem Cell Cloning", Genetic Engineering News, vol. 23, No. 7, (Apr. 1, 2003), pp. 17-18 & 68.

Khademhosseini, et al., "Microscale Technologies for Tissue Engineering and Biology", PNAS, vol. 103, No. 8, Feb. 21, 2006, pp. 2480-2487.

Kim, D., et al., "Glow Discharge Plasma Deposition (GDPD) Technique for the Local Controlled Delivery of Hirudin from Biomaterials", Pharmaceutical Research, 15(5), (1998), pp. 783-786.

Kim, Ung-Jin, et al., "Structure and Properties of Silk Hydrogels", Biomacromolecules, vol. 5(3), (2004), 786-792.

Kinart, et al., "Electrochemical Studies of 2-hydroxy-3-(3,4-dimethy1-9-oxo-9H-thioxanthen-2-yloxy)N,N,N-trimethyl-1-propanium chloride", J. Electroanal. Chem, 294, (1990), pp. 293-297.

Kipshidze, Nicholas, et al., "Therapeutic angiogenesis for critical limb ischemia to limit or avoid amputation", University of Wisconsin Medical School, The Journal of Invasive Cardiology, vol. 11, No. 1, (Jan. 1999), 25-28.

Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, (1997), pp. 159-192.

Klugherz, Bruce D., et al., "Gene delivery from a DNA controlled-release stent in porcine coronary arteries", Nature Biotechnology, vol. 18, (Nov. 2000), 1181-1184.

Kohilas, K, et al., "Effect of prosthetic titanium wear debris on mitogen-induced monocyte and lymphoid activation", John Hopkins University, Dept. of Orthopaedic Surgery, (Apr. 1999), 95-103.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.

Kwok, C., et al., "Design of Infection-Resistant Antibiotic-Releasing Polymers: I. Fabrication and Formulation", Journal of Controlled Release, 62, (1999), pp. 289-299.

Laboratory of Liposome Research, "Liposomes: General Properties", downloaded from the Internet on Feb. 9, 2006 at www.unizh.ch/onkwww/lipos.htm.

Laham, R. J., "Intrapericardial Delivery of Fibroblast Growth Factor-2 Induces Neovascularization in a Porcine Model of Chronic Myocardial Ischemia", J. Pharmacol Exper Therap, 292(2), (2000), pp. 795-802.

Leibovich, S. J., et al., "Macrophage-Induced Angiogenesis is Mediated by Tumour Necrosis Factor-α", Nature, vol. 329, (Oct. 15, 1987), pp. 630-632.

Leor, J., et al., "Bioengineered Cardiac Grafts—A New Approach to Repair the Infarcted Myocardium?", Circulation, 102[suppl III], (2000), pp. III-56-III-61.

Leor, J., et al., "Gene Transfer and Cell Transplant: An Experimental Approach to Repair a 'Broken Heart'", Cardiovascular Research, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at www.ncbi.nlm.nih.gov/entrez/query.fcgi?cmd=Retrieve&db=pubmed, (1995), pp. 695-703.

Lewin, B., "Repressor is Controlled by a Small Molecule Inducer", Genes VII, Oxford University Press, 7th ed., (2000), pp. 277-280.

Li, et al., "Cell Therapy to Repair Broken Hearts", Can. J. Cardiol., vol. 14, No. 5, (May 1998), pp. 735-744.

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, (2000), Chapter 33.

Li, J., et al., "PR39, A Peptide Regulator of Angiogenesis", Nature Medicine, 6(1), (Jan. 2000), pp. 49-55.

Li., Y. Y., et al., "Differential Expression of Tissue Inhibitors of Metalloproteinases in the Failing Human Heart", Circulation, 98(17), (1998), pp. 1728-1734.

Lindsey, M., et al., "Selective Matrix Metalloproteinase Inhibition Reduces Left Ventricular Remodeling but does not Inhibit Angiogenesis after Myocardial Infarction", Circulation, 105(6), (2002), pp. 753-758.

Long, D. M., et al., "Self-Cleaving Catalytic RNA", FASEB Journal, 7, (1993), pp. 25-30.

Lopez, J. J., et al., "Angiogenic potential of perivascular delivered aFGF in a porcine model of chronic myocardial ischemia", The American Physiological Society, 0363-6135/98, (1998), H930-H936.

Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, (1998), pp. 272-281.

Lu, L., et al., "Biodegradable Polymer Scaffolds for Cartilage Tissue Engineering", Clinical Orthopaedics and Related Research, Carl T. Brighton (ed.). No. 391S, (2001), pp. S251-S270.

Luo, Y., et al., "Cross-linked Hyaluronic Acid Hydrogel Films: New Biomaterials for Drug Delivery", Journal of Controlled Release, 69, (2000), pp. 169-184.

Lutolf, M, et al., "Synthesis and Physicochemical Characterization of End-Linked Poly(ethylene glycol)-co-peptide Hydrogels Formed by Michael-Type Addition", Biomacromolecules, vol. 4, (2003), 713-722.

Lyman, M. D., et al., "Characterization of the Formation of Interfacially Photopolymerized Thin Hydrogels in Contact with Arterial Tissue", Biomaterials, 17(3), (1996), pp. 359-364.

Mansour, S., et al., "Disruption of the proto-oncogene int-2 in mouse embryo-derived stem cells: a general strategy for targeting mutations to non-selectable genes", Nature, 336, (1988), pp. 348-352.

Martin, S. L., et al., "Total Synthesis and Expression in *Escherichia coli* of a Gene Encoding Human Tropoelastin", Gene, (1995), Abstract.

McDevitt, T., et al., "In vitro Generation of Differentiated Cardiac Myofibers on Micropatterned Laminin Surfaces", J. Biomed Mater Res., 60, (2002), pp. 472-479.

Meinel, L. et al., "The Inflammatory Responses to Silk Films In Vitro and In Vivo", Biomaterials, vol. 26, (2005), 147-155.

Narmoneva, D. A., et al., "Self-assembling short oligopeptides and the promotion of angiogenesis", Biomaterials, 26, (2005), 147-155.

Nazarov, R., et al., "Porous 3-D Scaffolds from Regenerated Silk Fibroin", Biomacromolecules, vol. 5(3), (2004), 718-726.

Nguyen, K. T., et al., "Photopolymerizable Hydrogels for Tissue Engineering Applications", Biomaterials, 23, (2002), pp. 4307-4314.

Nikolic, S. D., et al., "New Angiogenis Implant Therapy Improves Function of the Ischemic Left Venticle", Supplement to Circulation; Abstracts From Scientific Sessions 2000, 102(18), (Oct. 2000), pp. II-689, Abstract 3331.

Nikolic, Serjan D., et al., "Novel means to improve coronary blood flow", Clinical Science, Abstract from Scientific Sessions, (2000), II-689.

Nitinol Technical Information, "Ni-Ti Smart Sheets", downloaded from the Internet on Dec. 10, 2002 at: http://www.sma-inc.com/information.html, 1 page.

Nose, et al., "A novel cadherin cell adhesin molecule: its expression patterns associated with implantation and organogenesis of mouse embryos", Journal of Cell Biology, vol. 103 (No. 6, Pt. 2), The Rockefeller University Press, (Dec. 1986), 2649-2658.

Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), (1977), pp. 90-92.

Ozbas, B., et al., "Salt-Triggered Peptide Folding and Consequent Self-Assembly into Hydrogels with Tunable Modulus", Macromolecules, 37(19), (2004), pp. 7331-7337.

Ozbas-Turan, S., "Controlled Release of Interleukin-2 from Chitosan Microspheres", Journal of Pharmaceutical Sciences, 91(5), (May 2002), pp. 1245-1251.

Palmiter, R., et al., "Germ-Line Transformation of Mice", Ann. Rev. Genet., 20, 1986 465-499.

Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, (Jun. 2004).

Penta, K., et al., "Del1 Induces Integrin Signaling and Angiogenesis by Ligation of αVβ3", J. Biolog. Chem., 274(16), (Apr. 1999), pp. 11101-11109.

Perin, E. C., et al., "Transendocardial, Autologous Bone Marrow Cell Transplantation for Severe, Chronic, Ishemic Heart Failure", Circulation, (2003).

Pouzet, B., et al., "Is Skeletal Myoblast Transplantation Clinically Relevant in the Era of Angiotensin-Converting Enzyme Inhibitors?", Circulation, 104 [suppl I], (Sep. 2001), pp. 1-223-1-228.

Prather, et al., "Nuclear Transplantation in Early Pig Embryos", Biol. Reprod., 41, (1989), pp. 414-418.

Prosci Incorporated, "ILPIP (CT) Peptide".

Quellec, P., et al., "Protein Encapsulation Within Polyethylene Glycol-coated Nanospheres. I. Physicochemical Characterization", J. Biomed. Mater. Res., 42(1), (1998)), Abstract.

Ramirez-Solis, R., et al., "Gene Targeting in Embryonic Stem Cells", Methods in Enzymology, 225, (1993), pp. 855-878.

Ritter, A. B., et al., "Elastic modulus, distensibility, and compliance (capacitance)", Biomedical Engineering Principles, Chapter 4, (2005), 187-191.

Rowley, et al., "Alginate Hydrogels as Synthetic Extracelllular Matrix Materials", Biomaterials, 20(1), (1999), 45-53.

Sawhney, A. S., et al., "Bioerodible Hydrogels Based on Photopolymerized Poly(ethylene glycol)-co-poly(a-hydroxy acid) Diacrylate Macromers", Macromolecules, 26(4), (1993), pp. 581-587.

Sbaa-Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at www.stemcells.alphamedpress.org/cgi/content/full/20/6/585, 2002, 585-587.

Segura, T, et al., "Crosslinked Hyaluronic Acid Hydrogels: A Strategy to Functionalize and Pattern", Biomaterials, vol. 26 (4), (Feb. 2005), 359-371.

Segura, T, et al., "DNA delivery from hyaluronic acid-collagen hydrogels via a substrate-mediated approach", Biomaterials, vol. 26, 2005 1575-1584.

Segura, T., et al., "Substrate-Mediated DNA Delivery: Role of the Cationic Polymer Structure and Extent of Modification", Journal of Controlled Release, 93, (2003), pp. 69-84.

Segura, T., et al., "Surface-Tethered DNA Complexes for Enhanced Gene Deliver", Bioconjugate Chem, 13(3), (2002), pp. 621-629.

Shibasaki, F., et al., "Suppression of Signalling Through Transcription Factor NF-AT by Interactions Between Calcineurin and Bcl-2", Nature, 386(6626), Abstract downloaded from the Internet at www.ncbi.nlm.nih.gov/entrez/query.fcgi?CMD=Text&DB=pubmed, (1997).

Shin, H., et al., "Attachment, Proliferation, and Migration of Marrow Stromal Osteoblasts Cultured on Biomimetic Hydrogels Modified with an Osteopontin-Derived Peptide", Biomaterials, 25, 2004, pp. 895-906.

Shin, H., et al., "In vivo bone and soft tissue response to injectable, biodegradable oligo(poly(ethylene glycol) fumarate) hydrogels", Biomaterials 24, Elseview Science Ltd., (3201-3211), 2003.

Shu, Z, et al., "Disulfide-crosslinked hyaluronan-gelatin hydrogel films: a covalent mimic of the extracellular matrix for in vitro cell growth", Biomaterials, vol. 24(21), (Sep. 2003), 3825-3834.

Shu, Zheng, et al., "In situ crosslinkable hyaluronan hydrogels for tissue engineering", Biomaterials, vol. 25, No. 7-8, (Mar. 2004), 1339-1348.

Simons, M., et al., "Clinical trials in coronary angiogenesis: Issues, problems, consensus, an expert panel summary", Angiogenesis Research Center, American Heart Association, Inc.,, (Sep. 12, 2000), 1-14.

Spenlehauer, G, et al., "In vitro and in vivo degradation of poly(D,L lactide/glycolide) type microspheres made by solvent evaporation method", Biomaterials, vol. 10, (Oct. 1989), 557-563.

Spinale, F. G., "Matrix Metalloproteinases—Regulation and Dysregulation in the Failing Heart", Circ. Res., 90, (2002), pp. 520-530.

Springer, M., et al., "Angiogenesis Monitored by Perfusion with a Space-Filling Microbead Suspension", Mol. Ther., 1(1), Abstract downloaded from the Internet at www.ncbi.nlm.nih.gov/entrez/query.fcgi?cmd=Retrieve&db=PubMed, (2000), pp. 82-87.

Staatz, WD, et al., "Identification of a tetrapeptide recognition sequence for the alpha 2 beta 1 integrin in collagen", Journal of Biological Chemistry, 1991, 266(12), pp. 7363-7367.

Storm, G., et al., "Surface Modification of Nanoparticles to Oppose Uptake by the Mononuclear Phagocyte System", Advanced Drug Delivery Reviews, 17(1), Abstract downloaded from the Internet at www.sciencedirect.com, (Oct. 1995), pp. 31-48.

Strauer, B., et al., "Repair of Infarcted Myocardium by Autologous Intracoronary Mononuclear Bone Marrow Cell Transplantation in Humans", Circulation, 106, (2002), pp. 1913-1918.

Tybulewicz, V., et al., "Neonatal lethality and lymphopenia in mice with a homozygous disruption of the c-abl proto-oncogene", Cell, 65(7), Abstract downloaded from the Internet at www.sciencedirect.com, (Jun. 1991), pp. 1153-1163.

Unger, E. F., et al., "Effects of a Single Intracoronary Injection of Basic Fibroblast Growth Factor in Stable angina Pectoris", Am J. Cardiol, 85(12), Abstract downloaded from the Internet at www.sciencedirect.com, (Jun. 2000), pp. 1414-1419.

Van Der Giessen, Willem J., et al., "Marked inflammatory sequelae to implantation of biodegradable and nonbiodegradable polymers in porcine coronary arteries", Dept. of Cardiology, Erasmus University Rotterdam, Circulation, vol. 94, No. 7, (Oct. 1, 1996), 1690-1697.

Van Luyn, M. J., et al., "Cardiac Tissue Engineering: Characteristics of in Unison Contracting Two- and Three-Dimensional Neonatal Rat Ventricle Cell (Co)-Cultures", Biomaterials, 23, (2002), pp. 4793-4801.

Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at pubs.acs.org/cgi-bin/abstract.cgi/bcches/1997/8/i05/abs/bc9701095.html, (1997), pp. 686-694.

Visscher, G.E., et al., "Tissue response to biodegradable injectable microcapsules", Journal of Biomaterials Applications, vol. 2, (Jul. 1987), 118-119.

Vlodavsky, I., et al., "Extracellular Matrix-resident Basic Fibroblast Growth Factor: Implication for the Control of Angiogenesis", J. Cell Biochem, 45(2), Abstract downloaded from the Internet at www.ncbi.nlm.nih.gov/entrez/query.fcgi?cmd=Retrieve&db=PubMed, (Feb. 1991), pp. 167-176.

Wang, M., et al., "Mechanical Properties of Electrospun Silk Fibers", Macromolecules, vol. 37(18), (2004), 6856-6864.

Wasielewski, "Ischamische Erkrankungen, Gefassneubildung anregen", Deutsche Apotheker Zeitung, vol. 140, No. 3, Stuttgart (DE), (Jan. 20, 2000), 232-233.

Wilensky, R., et al., "Direct intraarterial wall injection of microparticles via a catheter: a potential durg delivery strategy following angioplasty", American Heart Journal, 122, (1991), p. 1136.

Witzenbichler, B., et al., "Vascular Endothelial Growth Factor-C (VEGF-C/VEGF-2) Promotes Angiogenesis in the Setting of Tissue Ischemia", AM Pathol., 153(2), (Aug. 1998), pp. 381-394.

Yager, P., et al., "Silk Protein Project", www.faculty.washington.edu/yagerp/silkprojecthome.html, (Aug. 23, 1997), pp. 1-16.

Yamamoto, N., et al., "Histologic evidence that basic fibroblast growth factor enhances the angiogenic effects of transmyocardial laser revascularization", Basic Research in Cardiology, vol. 95, No. 1, (Feb. 1, 2000), 55-63.

Yeo, L.Y., et al., "AC Electrospray Biomaterials Synthesis", Biomaterials, (2005), 7 pages.

Zervas, L., et al., "On Cysteine and Cystine Peptides. II. S-Acylcysteines in Peptide Synthesis", J. Am. Chem. Soc., 85(9), (May 1963), pp. 1337-1341.

Zheng, Shu, et al., "In situ crosslinkable hyaluronan hydrogels for tissue engineering", Biomaterials, Elsevier Science Publishers, vol. 25, No. 7-8, (2004), 1339-1348.

Zimmermann, W., et al., "Engineered Heart Tissue for Regeneration of Diseased Hearts", Biomaterials, 25, (2004), pp. 1639-1647.

Abbott Cardiovascular Systems, Non-Final Office Action dated Mar. 5, 2009 for U.S. Appl. No. 11/507,860.

Abbott Cardiovascular Systems, Non final office action dated Aug. 5, 2009 for U.S. Appl. No. 11/031,608.

Abbott Cardiovascular Systems, Final office action dated Mar. 29, 2010 for U.S. Appl. No. 11/031,608.

Abbott Cardiovascular Systems, Final Office Action mailed Jul. 15, 2010, U.S. Appl. No. 11/507,860.

Abbott Cardiovascular Systems, Final Office Action mailed Dec. 13, 2011 for U.S. Appl. No. 12/963,397.

Abbott Cardiovascular Systems, Final Office Action mailed Apr. 4, 2012 for U.S. Appl. No. 10/792,960.

Abbott Cardiovascular Systems, European Office Action mailed Apr. 11, 2012 for App No. 12155231.9, 9 pages.

Abbott Cardiovascular Systems, European Office Action mailed Apr. 10, 2012 for App No. 07810637.4, 6 pages.

Abbott Cardiovascular Systems, Final Office Action mailed May 9, 2012 for U.S. Appl. No. 11/110,223.

Abbott Cardiovascular Systems, European Search report for application No. 12151788.2 mailed Apr. 18, 2012, 6 pages.

Abbott Cardiovascular Systems, Non-final Office Action mailed Jun. 22, 2012 for U.S. Appl. No. 12/963,397.

Abbott Cardiovascular Systems, Restriction requirement mailed Jul. 3, 2012 for US 13/4722,324.

Abbott Cardiovascular Systems, Non-final Office Action mailed Jun. 26, 2012 for U.S. Appl. No. 12/632,612

Abbott Cardiovascular Systems, Japanese Office Action dated Jun. 11, 2012 for Appln. No. 2010-162711.

Abbott Cardiovascular Systems, Non-Final Office Action Sep. 11, 2012 for U.S. Appl. No. 10/792,960.

Abbott Cardiovascular Systems, Japanese office action dated Aug. 20, 2012 for JP 2009-537153.

Abbott Cardiovascular Systems, Non-Final Office Action dated Oct. 3, 2012 for U.S. Appl. No. 12/756,119.

Abbott Cardiovascular Systems, et al., Japanese Office Action dated Aug. 27, 2012 for JP 2009-522776.

Abbott Cardiovascular Systems, Final Office Action dated Nov. 8, 2012 for U.S. Appl. No. 12/114,717.

Abbott Cardiovascular Systems, Final Office Action mailed Nov. 7, 2012 for U.S. Appl. No. 10/781,984.

Abbott Cardiovascular Systems, Japanese Office Action dated Nov. 19, 2012 for Appln. No. 2009-539265.

Bull, S., et al., "Self-Assembled Peptide Amphiphile Nanofibers Conjugated to MRI Contrast Agents", Nano Letters, vol. 5, No. 1, (Jan. 2005), 4 pages.

Csonka, E., et al., "Interspecific Interaction of Aortic Endothelial and Smooth Muscle Cells", Acta Morphologica Hungarica, vol. 35, No. 1-2, (1987), 31-35.

Davis, M E., et al., "Injectable Self-Assembling Peptide Nanofibers Create Intramyocardial Microenvironments for Endothelial Cells", Circulation, 111, (2005), 442-450.

Griese, D. P., et al., "Vascular gene delivery of anticoagulants by transplantation of retrovirally-transduced endothelial progenitor cells", Cardiovascular Research, vol. 58, (2003), 469-477.

Hao, X, et al., "Angiogenic" Effects of Sequential release of VEGF-A 165 and PDGF-BB with Alginate Hydrogels After Myocardial Infarction, Cardiovascular Research, 75(1), (Apr. 6, 2007), 178-185.

Hartgerink, J. D, et al., "Peptide amphiphile nanofibers: A versatile scaffold for the preparation of self-assembling materials", PNAS, vol. 99, No. 8, (Apr. 16, 2002), 5133-5138.

Hartgerink, J. D., et al., "Self Assembly and Mineralization of Peptide-Amphiphile Nanofibers", Science, vol. 294, (Nov. 23, 2001), 1684-1688.

Li, B., et al., "VEGF and PlGF promote adult vasculogenesis by enhancing EPC recruitment and vessel formation at the site of tumor neovascularization", The FASEB Journal, vol. 20, (2006), 1495-1497.

Mogan, L., "Rationale of platelet gel to augment adaptive remodeling of the injured heart", J Extra Corpor Technol, 36(2), (Jun. 2004), 191-196.

Seeger, J. M., et al., "Improved in vivo endothelialization of prosthetic grafts by surface modification with fibronectin", J Vasc Surg, vol. 8, No. 4, (Oct. 1988), 476-82 (Abstract only).

Urbich, C., et aL, "Endothelial Progenitor Cells: Characterization and Role in Vascular Biology", Circulation Research, vol. 95, (2004), 343-353.

Zheng, W.,"Mechanisms of coronary angiogenesis in response to stretch; role of VEGF and TGF-Beta", Am J Physiol Heart Circ Physiol 280(2), (Feb. 2001), H909-H917.

\* cited by examiner

METHODS AND COMPOSITIONS FOR TREATING TISSUE USING SILK PROTEINS

CROSS-REFERENCE TO RELATED APPLICATION

The application is a divisional of co-pending U.S. patent application Ser. No. 11/566,643, filed Dec. 4, 2006 and incorporated herein by reference.

FIELD OF INVENTION

Tissue treatments and compositions.

BACKGROUND OF INVENTION

Ischemic heart disease typically results from an imbalance between the myocardial blood flow and the metabolic demand of the myocardium. Progressive atherosclerosis with increasing occlusion of coronary arteries leads to a reduction in coronary blood flow, which creates ischemic heart tissue. "Atherosclerosis" is a type of arteriosclerosis in which cells including smooth muscle cells and macrophages, fatty substances, cholesterol, cellular waste product, calcium and fibrin build up in the inner lining of a body vessel. "Arteriosclerosis" refers to the thickening and hardening of arteries. Blood flow can be further decreased by additional events such as changes in circulation that lead to hypoperfusion, vasospasm or thrombosis.

Myocardial infarction (MI) is one form of heart disease that results from the sudden lack of supply of oxygen and other nutrients. The lack of blood supply is a result of a closure of the coronary artery (or any other artery feeding the heart) which nourishes a particular part of the heart muscle. The cause of this event is generally attributed to arteriosclerosis in coronary vessels.

Formerly, it was believed that an MI was caused from a slow progression of closure from, for example, 95% then to 100%. However, an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Various procedures, including mechanical and therapeutic agent application procedures, are known for reopening blocked arteries. An example of a mechanical procedure includes balloon angioplasty with stenting, while an example of a therapeutic agent application includes administering a thrombolytic agent, such as urokinase. Such procedures do not, however, treat actual tissue damage to the heart. Other systemic drugs, such as ACE-inhibitors and Beta-blockers, may be effective in reducing cardiac load post-MI, although a significant portion of the population that experiences a major MI ultimately develop heart failure.

An important component in the progression to heart failure is remodeling of the heart due to mismatched mechanical forces between the infarcted region and the healthy tissue resulting in uneven stress and strain distribution in the left ventricle. Once an MI occurs, remodeling of the heart begins. The principle components of the remodeling event include myocyte death, edema and inflammation, followed by fibroblast infiltration and collagen deposition, and finally scar formation from extra-cellular matrix (ECM) deposition. The principle component of the scar is collagen which is non-contractile and causes strain on the heart with each beat. Non-contractility causes poor pump performance as seen by low ejection fraction (EF) and akinetic or diskinetic local wall motion. Low EF leads to high residual blood volume in the ventricle, causes additional wall stress and leads to eventual infarct expansion via scar stretching and thinning and border-zone cell apoptosis. In addition, the remote-zone thickens as a result of higher stress which impairs systolic pumping while the infarct region experiences significant thinning because mature myocytes of an adult are not regenerated. Myocyte loss is a major etiologic factor of wall thinning and chamber dilation that may ultimately lead to progression of cardiac myopathy. In other areas, remote regions experience hypertrophy (thickening) resulting in an overall enlargement of the left ventricle. This is the end result of the remodeling cascade. These changes also correlate with physiological changes that result in increase in blood pressure and worsening systolic and diastolic performance.

SUMMARY OF INVENTION

Compositions for forming a self-reinforcing composite biomatrix, methods of manufacture and use therefore are herein disclosed. Kits including delivery devices suitable for delivering the compositions are also disclosed. In some embodiments, the composition can include at least three components. In one embodiment, a first component can include a first functionalized polymer, a second component can include a second functionalized polymer and a third component can include silk protein or constituents thereof. In some embodiments, the composition can include at least one cell type and/or at least one growth factor. In some embodiments, the composition can include a biologic encapsulated, suspended, disposed within or loaded into a biodegradable carrier. In some embodiments, the composition(s) of the present invention can be delivered by a dual lumen injection device to a treatment area in situ, in vivo, as well as ex vivo applications.

DETAILED DESCRIPTION

Figure 1:
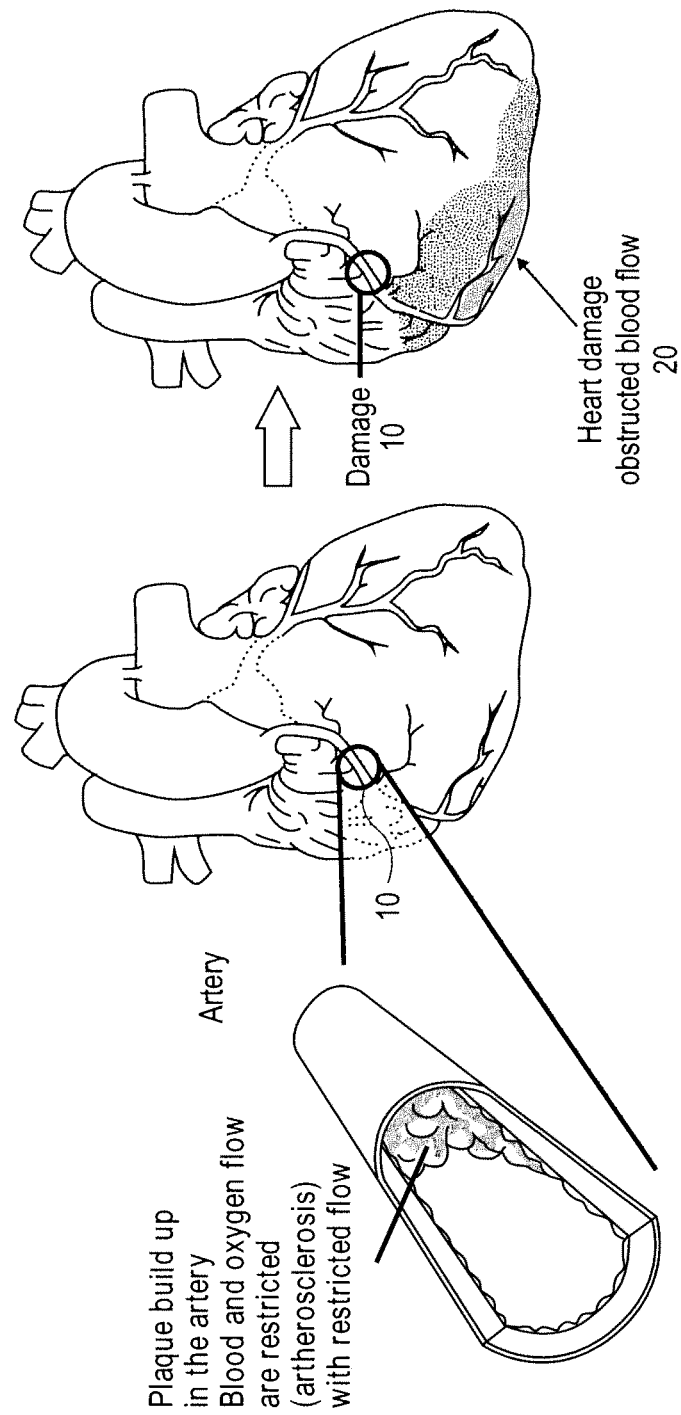
FIGS. 1A-1B illustrate the progression of heart damage once the build-up of plaque in an artery induces an infarct to occur.

FIGS. 1A-1B illustrate the progression of heart damage once the build-up of plaque induces an infarct to occur. FIG. 1A illustrates a site 10 where blockage and restricted blood flow can occur from, for example, a thrombus or embolus. FIG. 1B illustrates resultant damage area 20 to the left ventricle that can result from the lack of oxygen and nutrient flow carried by the blood to the inferior region left of the heart. Damage area 20 will likely undergo remodeling, and eventually scarring, resulting in a non-functional area.

A self-reinforcing composite matrix formed of three components and applied in situ to tissue for treatment or reparation of tissue damage, or to provide a support for sustained-delivery of a biologic, is herein disclosed. The composite matrix can include a two-component gelation system and a silk protein. "Bioscaffolding" and "two-component gelation system" and "gelation system" are hereinafter used interchangeably. Examples of two-component gelation systems include, but are not limited to, alginate construct systems, fibrin glues and fibrin glue-like systems, self-assembled peptides, synthetic polymer systems and combinations thereof. The gelation system can provide a rapidly degrading matrix for a slower degrading constituent, such as, for example, silk protein. Over time, the silk protein can form a self-reinforcing composite matrix. The components of the composite matrix, in various combinations, may be co-injected to an infarct region by a dual-lumen delivery device. Examples of dual-lumen delivery devices include, but are not limited to, dual syringes, dual-needle left-ventricle injection devices, dual-needle transvascular wall injection devices and the like.

In some applications, the two-component gelation system includes fibrin glue. Fibrin glue consists of two main components, fibrinogen and thrombin. Fibrinogen is a plasma glycoprotein of about 340 kiloDaltons (kDa) in its endogenous state. Fibrinogen is a symmetrical dimer comprised of six paired polypeptide chains, alpha, beta and gamma chains. On the alpha and beta chains, there is a small peptide sequence called a fibrinopeptide which prevents fibrinogen from spontaneously forming polymers with itself. In some embodiments, fibrinogen is modified with proteins. Thrombin is a coagulation protein. When combined in equal volumes, thrombin converts the fibrinogen to fibrin by enzymatic action at a rate determined by the concentration of thrombin. The result is a biocompatible gel which gelates when combined at the infarct region. Fibrin glue can undergo gelation between about 5 to about 60 seconds. Examples of fibrin glue-like systems include, but are not limited to, Tisseel™ (Baxter), Beriplast P™ (Aventis Behring), Biocol® (LFB, France), Crosseal™ (Omrix Biopharmaceuticals, Ltd.), Hemaseel HMN® (Haemacure Corp.), Bolheal (Kaketsuken Pharma, Japan) and CoStasis® (Angiotech Pharmaceuticals).

In some applications, a two-component gelation system is a synthetic polymer system. Examples of synthetic polymers include, but are not limited to, polyamino acids, polysaccharides, polyalkylene oxide or polyethylene glycol (PEG). The molecular weight of the compounds can vary depending on the desired application. In most instances, the molecular weight (mw) is about 100 to about 100,000 mw. When the core material is polyethylene glycol, the molecular weight of the compound(s) is/are about 7,500 to about 20,000 mw and more preferably, about 10,000 mw. When combined together, synthetic polymers can form a hydrogel depending on the abundancy of reactive groups, among other parameters. A "hydrogel" is a network of polymer chains that are hydrophilic, sometimes found as a colloidal gel in which water is the dispersion medium. Hydrogels are super-absorbent (they can contain over 99% water) and can be comprised of natural or synthetic polymers.

In some embodiments, the two-component gelation system includes polyethylene glycols. PEG is a synthetic polymer having the repeating structure $(OCH_2CH_2)_n$. A first component may be a polyethylene glycol (PEG) polymer functionalized with at least two nucleophilic groups. Examples of nucleophilic groups include, but are not limited to, thiol (—SH), thiol anion (—S$^-$), and amine (—NH$_2$). A "nucleophile" is a reagent which is attracted to centers of positive charge. A nucleophile participates in a chemical reaction by donating electrons to an electrophile in order to form a chemical bond. A second component may be a PEG polymer functionalized with at least two electrophilic groups. Examples of electrophilic groups include, but are not limited to, N-hydroxy succinimide ester (—NHS), acrylate, vinyl sulfone, and maleimide. —NHS, or succinimidyl, is a five-member ring structure represented by the chemical formula —N(COCH$_2$)$_2$. An "electrophile" is a reagent attracted to electrons that participates in a chemical reaction by accepting an electron pair in order to bond to a nucleophile. The total number of electrophilic and nucleophilic groups should be greater than four.

Some inherent characteristics of unmodified hydrogels include, but are not limited to, its ability to swell and its ability to rapidly gel. As used herein, the term "unmodified" means hydrogels in which no other constituents are added thereto. These characteristics can contribute to rapid degradation of the hydrogel. In addition, in situ gelling hydrogels generally exhibit weak mechanical properties, resulting in poor implant integrity In some applications, however, these same characteristics (e.g., swelling) can be harmful. For example, if applied to an organ such as the heart to treat a post-infarct myocardial region, swelling should be minimized to reduce or eliminate excess pressure on the treatment region. Additionally, in some applications, a less rapid degradation may be desirable.

In some embodiments, two functionalized PEGs comprising a PEG functionalized with at least two nucleophilic groups and a PEG functionalized with at least two electrophilic groups can be combined in a 1:1 ratio. The PEGs can be stored in a 0.01M acidic solution at a pH below about 4.0. At room temperature and standard concentration, reaction and cross-linking between the two functionalized PEGs occurs beginning at approximately pH greater than 6.5. Under these conditions, reaction kinetics are slow. When 0.3 M basic buffer solution at pH about 9.0 is added to the PEGs, gelation occurs in less than 1 minute. This system exhibits poor cytocompatibility due to the low pH of the functionalized PEG solution and the high osmolality pH 9.0 buffer. "Cytocompatibility" refers to the ability of media to provide an environment conducive to cell growth. Additionally, this system does not include any cell adhesion ligands.

The reaction of the functionalized PEGs in forming a gel can occur by a number of different chemical reactions depending on the functionality of the groups attached to the PEGs. For example, the gel can be formed by a Michael-type addition reaction or a condensation reaction. In general, a Michael-type addition reaction involves the reaction of an α,β-unsaturated carbonyl with a nucleophile. A Michael-type addition reaction can occur at a pH greater than about 6.8. Michael addition reactions are well known by those skilled in the art. Examples of moieties on functionalized PEGs which can undergo a Michael's addition reaction include, but are not limited to: PEG-SH combined with PEG-maleimide; and PEG-SH combined with PEG-acrylate. In some embodiments, the reaction could be activated with a buffer with a pH greater than about 4, by a catalytic amount of various amines or a combination thereof. A condensation reaction is a chemical reaction in which two molecules or moieties react and become covalently bonded to one another by the concurrent loss of a small molecule, often water, methanol, or a type of hydrogen halide such as hydrogen chloride. In polymer chemistry, a series of condensation reactions can take place whereby monomers or monomer chains add to each other to form longer chains. Examples of moieties on functionalized PEGs which can undergo a condensation reaction include, but are not limited to, PEG-NHS ester and PEG-NH$_2$. It is anticipated that a Michael addition reaction would contribute to the long term stability of the resulting gel since thioether bonds are formed as compared to the more hydrolytically labile thioester bonds formed from the reaction of thiols with activated esters.

Silk fibers from spiders (e.g., *Nephila clavipes* and *Araneus diadematus*) and silkworms (e.g., *Bombyx mori*) represent the strongest natural fibers currently known. Their mechanical properties include high strength and toughness and are derived from a highly controlled self-assembly path through liquid crystalline phases leading to highly stable materials. Silk from *B. mori* consists primarily of two protein components, fibroin and sericin. Fibroin, or silk protein, is the structural protein in silk fibers and sericin is the water-soluble glue that binds fibroin fibers together. Fibroin protein consists of light and heavy chain polypeptides of approximately 350 kDa and 25 kDa, respectively. The principal constituent of silk fibers, i.e., silk proteins, can undergo self-assembly into insoluble β-sheets. The β-sheets have been shown to exhibit a high level of organization. The β-sheets have also been shown to be numerous and very small and contained within the heavy chain. Compared to synthetic polymers, which are made of one or two repeating monomer units polymerized to a broad range of lengths, biological polymers such as silk fibroin are identical molecules of great complexity made up of almost 20 different amino acid monomers. Natural silk can be made at room temperature from an aqueous solution, which methods are known in the art.

The United States Pharmacopeia defines silk as non-degradable because it retains greater than 50% of its tensile integrity 60 days post-implantation in vivo. Within the period of a year, silk has been shown to proteolytically degrade and resorb when applied in vivo. Recent experiments have shown that silk is a mechanically robust biomaterial with predictable long-term degradation characteristics. See, e.g., R. L. Horan, et al., *In vitro degradation of silk fibroin*, Biomaterials 26 (2005) 3385-3393. It is anticipated that silk matrices formed from silk proteins have the potential for many different types of medical treatments.

In some embodiments, a silk protein or a block-copolymer of silk protein (hereinafter, collectively referred to as "silk protein") can be combined with a two-component gelation system to form a self-reinforcing composite matrix. A block co-polymer of silk protein can be, for example, silk-elastin (available from Protein Polymer Technologies, Inc., California), silk-collagen or silk-laminin, or any peptide sequence of elastin, collagen or laminin conjugated with a silk protein. In some embodiments, a glycosoaminoglycan (GAG) such as, for example, hyaluronic acid, heparin sulfate, chondroitin sulfate or keratin sulfate can be conjugated with a block-copolymer of silk protein. The matrix can be used in a variety of medical treatment applications including, but not limited to, cell delivery, a platform for neo tissue formation, cartilage repair, spinal repair, treatment of hernias, organ adhesion prevention, use as a biosurgical adhesive and/or post-myocardial infarction treatment. Combined with unmodified hydrogels such as, but not limited to, fibrin glue and functionalized PEGs, it is anticipated that the silk protein will reduce or eliminate swelling of the hydrogel and increase its mechanical stability. In addition, a silk matrix has a very porous structure. Salt leaching and gas foaming are known to produce silk protein matrices with porosity greater than 100 µm, which is generally considered to be the minimum porosity for cell migration and expansion. Nazarov, R., et al., *Porous 3-D Scaffolds from Regenerated Silk Fibroin*, Biomacromolecules 2004, 5, 718-719. The structure of a silk matrix can allow for controlled release of a substance, including, but not limited to, biologics such as therapeutic agents, cells and growth factors.

In some embodiments, at least two functionalized PEGs with a total functionality greater than four can be combined with a silk protein in solution to form a self-reinforcing composite matrix. "Functionality" refers to the number of electrophilic or nucleophilic groups on the polymer core which are capable of reacting with other nucleophilic or electrophilic groups, respectively, to form a gel. For example, a first functionalized PEG may be thiol PEG, or amino PEG wherein the first functionalized PEG includes at least two nucleophilic groups. A second functionalized PEG may be N-hydroxy succinimide ester PEG, acrylate PEG, vinyl sulfone PEG or maleimide PEG wherein the second functionalized PEG includes at least two electrophilic groups. In some embodiments, the first functionalized PEG and the second functionalized PEG may be combined in a 1:1 ratio. In other embodiments, the first functionalized PEG and the second functionalized PEG may be combined in a less than 1:1 ratio.

In some embodiments, the combination (i.e., the functionalized PEGs) can be stored in a solid or liquid phase. In one embodiment, the combination is stored in a solid phase. Approximately 2 hours before delivery, an acidic aqueous solution can be added to the functionalized PEGs to form a liquid phase. The solution may be, for example, a dilute hydrochloric acid solution in a pH range of about 3.5 to about 4.5. An acidic environment may be appropriate for PEG-NHS esters. In some embodiments, a neutral pH aqueous solution can be appropriate for PEG-NHS esters. A basic environment may be appropriate for thiol PEG or amino PEG.

At or close to the time of delivery, a silk protein in aqueous solution may be added to the acidic or neutral functionalized PEG solution. For PEGs stored in a basic environment, the silk protein may to co-delivered in situ. The silk protein can be up to 50 mass percent of the combined PEGs. In some embodiments, the silk protein is 10 mass percent of the combined PEGs.

In some embodiments, the functionalized PEGs can be combined with a silk protein in a solid phase. Approximately 2 hours before delivery, an aqueous solution can be added to the combination to form a liquid phase. At or close to the time of delivery, a high pH buffer solution of about 7.5 to about 9.5 may be added to initiate the gelation process. For example, basic buffers can include sodium phosphate and sodium carbonate buffers at a concentration of about 100 mM to about 300 mM. For PEG-NHS esters, a stoichiometric amount of base can be added. For vinyl sulfone or acrylate PEGs, a catalytic amount of base can be added. The silk protein can be up to 50 mass percent of the combined PEGs. In some embodiments, the silk protein is 10 mass percent of the combined PEGs.

In some embodiments, components of fibrin glue can be combined with a silk protein to form a self-reinforcing composite matrix. Fibrin glue may include fibrinogen or a fibrinogen-like compound and thrombin. The silk protein may be combined with fibrin glue in a similar manner as that described with respect to the PEGs.

In some embodiments, a cell type can be added to the self-reinforcing composite matrix. Examples of cell types include, but are not limited to, localized cardiac progenitor cells, mesenchymal stem cells (osteoblasts, chondrocytes and fibroblasts), bone marrow derived mononuclear cells, adipose tissue derived stem cells, embryonic stem cells, umbilical-cord-blood-derived stem cells, smooth muscle cells or skeletal myoblasts. In some embodiments, a growth factor can be added to the self-reinforcing composite matrix. Examples of growth factors include, but are not limited to, isoforms of vasoendothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, follistatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). In some applications, the functionalized PEGs can react with the growth factors which could stabilize the growth factors, extend their half-life or provide a mode for controlled release of the growth factors. The growth factors can act to help survival of injected hMSC or endogenous progenitor cells of the infarct region. In addition, the growth factors can aid in homing endogenous progenitor cells to the injury site.

In some embodiments, a biologic such as a growth factor or pharmaceutical can be encapsulated, suspended, disposed within or loaded into a biodegradable carrier and combined with at least one component of a two-component gel system and silk protein for sustained-release and/or controlled delivery to a target site. An example of a suitable biologic includes, but is not limited to, IGF-1, HGF, VEGF, bFGF, stem cell factor (SCF), G-CSF, PDGF or other growth factor. In one embodiment, the biologic is IGF-1. IGF-1 is known for its pro-survival and anti-apoptotic effects, among other characteristics. It is known that IGF-1 has beneficial effects on acute MI and chronic heart failure by affecting endogenous cardiac cells. Since IGF-1 has a short in vivo half-life, treatment can be enhanced by providing controlled release of IGF-1 from a biodegradable carrier or self-reinforcing composite matrix.

In one embodiment, the biodegradable carrier is an electrospun absorbable nanofiber or microfiber, hereinafter referred to interchangeably. A nanofiber can be in a range of between about 40 nm and about 2000 nm, while a microfiber can be in a range of between about 1 µm and about 10 µm. In one embodiment, the biologic (or no biologic) infused microfiber can be formulated by electrospinning. "Electrospinning" is a process by which microfibers are formed by using an electric field to draw a polymer solution from the tip of a reservoir with a nozzle to a collector. The nozzle can be a single nozzle or a coaxial nozzle. A voltage is applied to the polymer solution which causes a stream of solution to be drawn toward a grounded collector. Electrospinning generates a web of fibers which can be subsequently processed into smaller lengths. For example, the fibers can be cryogenically milled using a high frequency ball or centrifugal mill.

Examples of polymers which may be used to form the electrospun microfibers generally include, but are not limited to, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly(ε-caprolactone) (PCL), polydioxanone, PEG-PLGA diblock and PEG-PLGA-PEG triblock copolymers, and poly(ester amides) (PEA).

Additionally, polymers which may be used to form elastomeric electrospun microfibers include, but are not limited to, biodegradable poly(ester urethanes) (PEU), poly(ester urethane) ureas (PEUU), polyhydroxyalkanoates such as poly(4-hydroxybutyrate) or poly(3-hydroxybutyrate), PCL-PLA copolymers, PCL-PGA copolymers, poly(1,3-trimethylene carbonate) (PTMC), PTMC-PLA, and PTMC-PCL copolymers. Elastomeric microfibers have been demonstrated to possess mechanical anisotropy similar to native tissue.

Additionally, the polymers described above can be used to form core-shell electrospun microfibers. Core-shell electrospun microfibers can be formed by using a coaxial nozzle in the electrospinning process. For example, two different polymer solutions can be placed in two separate coaxial reservoirs with one common nozzle. When the electrospinning process is started, the polymer solutions will only come into contact at the nozzle tip, resulting in a fiber within a tube morphology. Core-shell electrospun microfibers can be useful for reduction of burst release and sequential biologics release profiles. "Burst" refers to the amount of agent released in one day or any short duration divided by the total amount of agent (which is released for a much longer duration). A sequential biologics release profile is the case when a first biologic is added to the first polymer solution and a second biologic is added to the second polymer solution. Depending on which polymer solution forms the "core" or "shell", the biologic in the "shell" (outer tube) will be released prior to the biologic in the "core" (inner fiber). In this manner, the application of two different types of biologics can be controlled.

In another embodiment, the biodegradable carrier is a microparticle, or microsphere, hereinafter referred to interchangeably. Various methods can be employed to formulate and infuse or load the microparticles with the biologic. In some embodiments, the microparticles are prepared by a water/oil/water (W/O/W) double emulsion method. In the first phase, an aqueous phase containing the biologic is dispersed into the oil phase consisting of polymer dissolved in organic solvent (e.g., dichloromethane) using a high-speed homogenizer. Examples of sustained-release polymers which may be used include those polymers described above. The primary water-in-oil (W/O) emulsion is then dispersed to an aqueous solution containing a polymeric surfactant, e.g., poly (vinyl alcohol) (PVA), and further homogenized to produce a W/O/W emulsion. After stirring for several hours, the microparticles are collected by filtration. In other embodiments, the microparticles can be prepared by an electrospray method. Such methods are known by those skilled in the art. See, e.g., Yeo, L. Y. et al., *AC electrospray biomaterials synthesis*, Biomaterials. 2005 November; 26(31):6122-8.

Example 1

A first component is a 10% solution of PEG thiol in carbonate and/or phosphate buffer adjusted to pH between 8 and 9. The buffer can be between 140 mM and 160 mM. The PEG thiol can be PTE-200SH, molecular weight 20,000 kD available from NOF corporation, Japan. A second component is a 10% to 13% solution of PEG NHS in phosphate buffer at physiological pH. The PEG NHS can be PTE-200GS, molecular weight 20,000 kD available from NOF corporation, Japan. The amount of oligomer component in solution can vary from 2% to 20% by weight, however stoichiometry between the first component and the second component should be close to 1:1 to assure reaction between the components. An aqueous solution of silk protein (synthetic or non-synthetic) can be added to the first component for a final concentration of 50 mg/mL. The aqueous silk protein solution should be kept at between 3° C. and 9° C., preferably between 4° C. and 8° C. Prior to addition of the aqueous silk protein to the first component, a biologic including a growth factor and/or pharmaceutical encapsulated, suspended, disposed within or loaded into a biodegradable carrier can be added to the aqueous silk protein solution. The biodegradable carrier can be formulated according to embodiments of the present invention. Just prior to injection to a treatment site, a cell suspension including between about 0.5 million and about 10 million cells can be added to the second component. Each injection can be between 100 µL to 200 µL combined for up to 25 injections.

Example 2

A first component is a 10% solution of PEG amine in carbonate or phosphate buffer adjusted to pH between 8 and 9. The buffer can be between 140 mM and 160 mM, preferably 150 mM. The PEG amine can be PTE-200PA, molecular weight 20,000 kD available from NOF corporation, Japan. A second component is a 10% to 13% solution of PEG NHS in phosphate buffer at physiological pH. The PEG NHS can be PTE-200GS, molecular weight 20,000 kD available from NOF corporation, Japan. The amount of oligomer component in solution can vary from 2% to 20% by weight, however stoichiometry between the first component and the second component should be close to 1:1 to assure reaction between the components. An aqueous solution of silk protein (synthetic or non-synthetic) can be added to the first component for a final concentration of 50 mg/mL. The aqueous silk protein solution should be kept at between 3° C. and 5° C., preferably 4° C. Prior to addition of the aqueous silk protein to the first component, a biologic including a growth factor and/or pharmaceutical encapsulated, suspended, disposed within or loaded into a biodegradable carrier can be added to the aqueous silk protein solution. The biodegradable carrier can be formulated according to embodiments of the present invention. Just prior to injection to a treatment site, a cell suspension including between about 0.5 million and about 10 million cells can be added to the second component. Each injection can be between 100 µL to 200 µL combined for up to 25 injections.

Example 3

A first component is a 10% solution of PEG thiol in carbonate or phosphate buffer adjusted to pH between 8 and 9. The buffer can be between 140 mM and 160 mM. The PEG thiol can be PTE-200SH, molecular weight 20,000 kD available from NOF corporation, Japan. A second component is a 4% to 5% solution of PEG diacrylate in phosphate buffer. The PEG diacrylate can be poly(ethylene glycol)diacrylate, molecular weight 4000 kD available from Polysciences, Inc., Pennsylvania, U.S.A. The amount of oligomer component in solution can vary from 2% to 20% by weight, however stoichiometry between the first component and the second component should be close to 1:1 to assure reaction between the components. An aqueous solution of silk protein (synthetic or non-synthetic) can be added to the first component for a final concentration of 50 mg/mL. The aqueous silk protein solution should be kept at between 3° C. and 9° C., preferably between 4° C. and 8° C. Prior to addition of the aqueous silk protein to the first component, a biologic including a growth factor and/or pharmaceutical encapsulated, suspended, disposed within or loaded into a biodegradable carrier can be added to the aqueous silk protein solution. The biodegradable carrier can be formulated according to embodiments of the present invention. Just prior to injection to a treatment site, a cell suspension including between about 0.5 million and about 10 million cells can be added to the second component. Each injection can be between 100 µL to 200 µL combined for up to 25 injections.

In any of the above examples, an additional two-component gel can be combined with the oligomers. For example, sodium hyaluronate, available from Genzyme Advanced Biomaterials, Massachusetts, U.S.A., can be combined with the oligomers. Sodium hyaluronate provides a ligand to the CD 44 receptor on hMSCs. The CD44 receptor is a transmembrane glycoprotein expressed on a variety of cells like endothelial, epithelial and smooth muscle cells. This molecule has many important functions, including cell-cell and cell-matrix interactions and signal transduction. In one embodiment, hyaluronic acid is a solution between about 0.01% and 0.5%. Additionally, in some embodiments, an extracellular matrix polymer, such as collagen, can be the first component.

Figure 2:
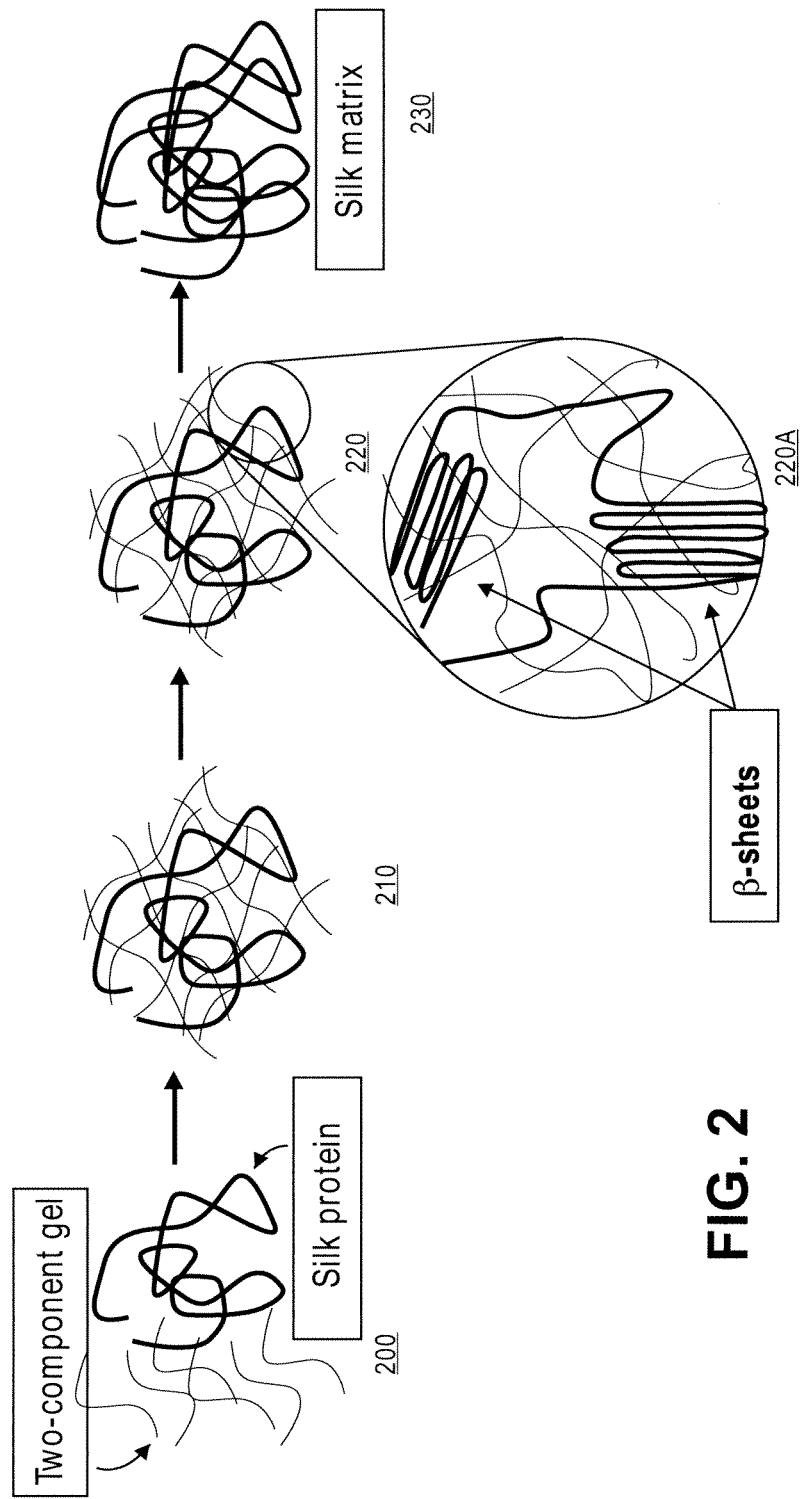
FIG. 2 illustrates a representation of an embodiment of forming a self-reinforcing composite matrix including a two-component gelation system and a silk protein.

FIG. 2 illustrates a representation of an embodiment of forming a self-reinforcing composite matrix including a two-component gelation system and a silk protein. In some embodiments, a first functionalized PEG and a second functionalized PEG, which are precursors of the two-component gelation systems, are combined with a silk protein (200). The combination starts an initial cross-linking reaction between the PEGs forming a hydrogel reaches the gel point from about 2 seconds to about 120 seconds (210). Precipitation and formation of β-sheets and crystallization of the silk protein begins to occur immediately upon mixing and may continue for up to 48 hours. (220). As the silk proteins begin to self-assemble, it becomes less and less soluble in solution; however, the silk protein assembly is locked within the hydrogel. The β-sheets can be numerous and very small (220a). Between about 0 days and about 30 days, degradation and dissolution of the gel occurs (230). In some embodiments, degradation of the gel occurs between about 0.5 to about 1 day. On the other hand, the silk protein matrix degrades within about 60 days to about 365 days. As a result, a self-reinforcing composite matrix comprised of silk protein remains at the treatment site, gradually degrading over time. In some embodiments, at least one cell type and/or a biologic such as a cell type or a growth factor encapsulated, suspended, disposed within or loaded into a biodegradable carrier is added to the self-reinforcing composite matrix. The biodegradable carrier can be formulated according to embodiments of the present invention. Advantageously, the addition of silk protein to the hydrogel substantially controls precipitation, i.e., phase separation, and swelling. For these silk hydrogels, tensile strength of the silk is about 1.1 GPa to about 1.4 GPa. In addition, for those embodiments which include a cell type and/or biodegradable carrier including a biologic, the silk matrix reinforces the mechanical property of the hydrogel and control matrix structure.

The compositions described herein can be used in medical treatment applications in which hydrogels can contribute beneficially, but swelling is not desired (an inherent characteristic of unmodified hydrogels). For example, the resulting self-reinforcing composite matrix can be used for cell delivery in a necrosed or compromised organ or tissue region, or, as a platform for cells to grow and form neo tissue. It is anticipated that the silk matrix will degrade at a treatment site at a rate substantially slower than an unmodified hydrogel system, thus enabling cells to proliferate longer, or, allowing for a more controlled release of cells within the matrix to the treatment region. Additionally, the slower degrading platform of the silk protein can allow for a more sustained and/or controlled release of a biologic encapsulated in, suspended, disposed within or loaded into a biodegradable carrier, which can be added to the precursor silk protein aqueous solution prior to delivery to a treatment region. Silk protein naturally degrades between about 60 days and 365 days. Thus, as the silk protein matrix degrades over time, it is anticipated that the biodegradable carrier will slowly diffuse out of the matrix and into the treatment site. Since the biologic also must diffuse out from the biodegradable carrier, the compositions described in embodiments of the present invention can allow for a sustained-release of treatment agent to the treatment region without the patient having to undergo multiple invasive procedures. In vivo, in vivo and in situ applications are contemplated in the present invention.

Methods of Use

In some embodiments, the self-reinforced composite matrix is delivered to a post-myocardial infarct region or other treatment region. The viscosity of the precursors, i.e., aqueous solutions of the two-component gelation system, silk protein and buffer, can be in a range from about 5 centipoise to about 70 centipoise. Devices which can be used to deliver each component of the gel include, but are not limited to, minimally invasive injection devices such as dual-needle left-ventricle injection devices and dual-needle transvascular wall injection devices, and dual syringes. Methods of access to use the minimally invasive injection devices (i.e., percutaneous or endoscopic) include access via the femoral artery or the subxiphoid. "Xiphoid" or "xiphoid process" is a pointed cartilage attached to the lower end of the breastbone or sternum, the smallest and lowest division of the sternum. Both methods are known by those skilled in the art.

Figure 3:
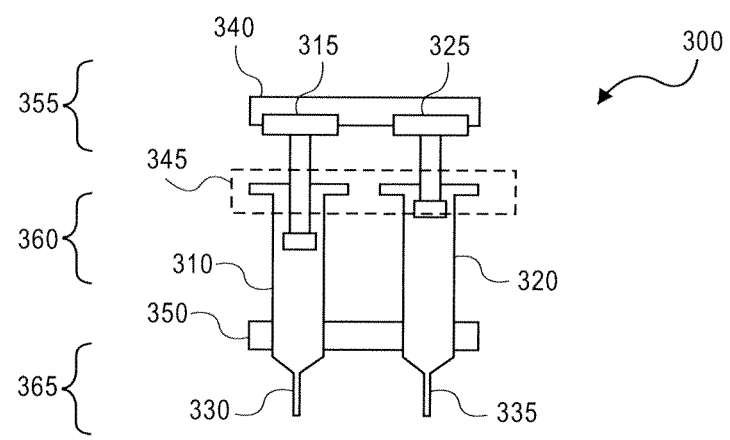
FIG. 3 illustrates an embodiment of a dual bore delivery device.

FIG. 3 illustrates an embodiment of a dual syringe device which can be used to deliver the compositions of the present invention. Dual syringe 300 can include first barrel 310 and second barrel 320 adjacent to one another and connected at a proximal end 355, distal end 360 and middle region 365 by plates 340, 345 and 350, respectively. In some embodiments, barrels 310 and 320 can be connected by less than three plates. Each barrel 310 and 320 includes plunger 315 and plunger 325, respectively. Barrels 310 and 320 can terminate at a distal end into needles 330 and 335, respectively, for extruding a substance. In some embodiments, barrels 310 and 320 can terminate into cannula protrusions for extruding a substance. Barrels 310 and 320 should be in close enough proximity to each other such that the substances in each respective barrel are capable of mixing with one another to form a bioscaffolding in the treatment area, e.g., a post-infarct myocardial region. Dual syringe 300 can be constructed of any metal or plastic which is minimally reactive or completely unreactive with the formulations described in the present invention. In some embodiments, dual syringe 300 includes a pre-mixing chamber attached to distal end 365.

In some applications, first barrel 310 can include a first mixture including precursors of a two-component gelation system in solid phase wherein an aqueous solution of silk is added prior to delivery. The pH of the solution in first barrel 310 can be between 2 and 6.5 (for PEG-nucleophile with PEG-electrophile), or 5 and 7 (fibrinogen). In neutral pH, a cell suspension can be added to first barrel 310 just prior to delivery. Second barrel 320 can include a basic buffer or thrombin according to any of the embodiments described previously. A therapeutic amount of the resulting self-reinforcing composite matrix can be between about 25 µL to about 200 µL, preferably about 50 µL. In some applications, first barrel 310 includes a first basic buffer solution combined with a first functionalized polyethylene glycol with nucleophilic groups forming a 10% weight/volume solution at a pH between 8 and 9 and second barrel 320 includes a second buffer solution combined with a second functionalized polyethylene glycol with electrophilic groups forming a 4% to 13% weight/volume solution at a physiological pH. First barrel 310 can further include a biologic encapsulated, suspended, disposed within or loaded into a biodegradable carrier suspended within an aqueous solution of silk protein. In one embodiment, the biologic is IGF-1. When the contents of barrel 310 and barrel 320 are combined in situ or in vivo, a self-reinforcing composite matrix may form at the treatment region. Dual syringe 300 can be used during, for example, an open chest surgical procedure.

Figure 4A:
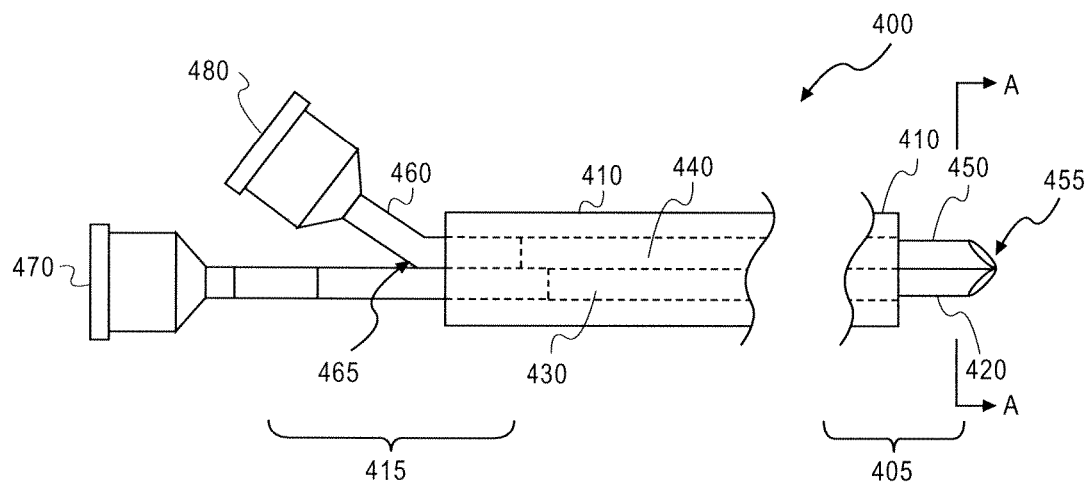
FIGS. 4A-4B illustrate an alternative embodiment of a dual bore delivery device.
Figure 4B:
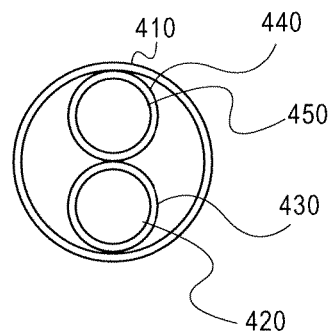

FIGS. 4A-4B illustrate an embodiment of a dual-needle injection device which can be used to deliver the compositions of the present invention. Delivery assembly 400 includes lumen 410 which may house delivery lumens, guidewire lumens and/or other lumens. Lumen 410, in this example, extends between distal portion 405 and proximal end 415 of delivery assembly 400.

In one embodiment, delivery assembly 400 includes first needle 420 movably disposed within delivery lumen 430. Delivery lumen 430 is, for example, a polymer tubing of a suitable material (e.g., polyamides, polyolefins, polyurethanes, etc.). First needle 420 is, for example, a stainless steel hypotube that extends a length of the delivery assembly. First needle 420 includes a lumen with an inside diameter of, for example, 0.08 inches (0.20 centimeters). In one example for a retractable needle catheter, first needle 420 has a needle length on the order of about 40 inches (about 1.6 meters) from distal portion 405 to proximal portion 415. Lumen 410 also includes auxiliary lumen 440 extending, in this example, co-linearly along the length of the catheter (from a distal portion 405 to proximal portion 415). Auxiliary lumen 440 is, for example, a polymer tubing of a suitable material (e.g., polyamides, polyolefins, polyurethanes, etc.). At distal portion 405, auxiliary lumen 440 is terminated at a delivery end of second needle 450 and co-linearly aligned with a delivery end of needle 420. Auxiliary lumen 440 may be terminated to a delivery end of second needle 450 with a radiation-curable adhesive, such as an ultraviolet curable adhesive. Second needle 450 is, for example, a stainless steel hypotube that is joined co-linearly to the end of main needle 420 by, for example, solder (illustrated as joint 455). Second needle 450 has a length on the order of about 0.08 inches (0.20 centimeters). FIG. 4B shows a cross-sectional front view through line A-A' of delivery assembly 400. FIG. 4B shows main needle 420 and second needle 450 in a co-linear alignment.

Referring to FIG. 4A, at proximal portion 415, auxiliary lumen 440 is terminated to auxiliary side arm 460. Auxiliary side arm 460 includes a portion extending co-linearly with main needle 420. Auxiliary side arm 460 is, for example, a stainless steel hypotube material that may be soldered to main needle 420 (illustrated as joint 465). Auxiliary side arm 460 has a co-linear length on the order of about, in one example, 1.2 inches (3 centimeters).

The proximal end of main needle 420 includes adaptor 470 for accommodating a substance delivery device (e.g., a component of a two-component bioerodable gel system). Adaptor 470 is, for example, a molded female luer housing. Similarly, a proximal end of auxiliary side arm 460 includes adaptor 480 to accommodate a substance delivery device (e.g., a female luer housing).

The design configuration described above with respect to FIGS. 4A-4B is suitable for introducing two-component gel compositions of the present invention. For example, a gel may be formed by a combination (mixing, contact, etc.) of a first component and a second component according to embodiments of the present invention previously described. Representatively, a first component may be introduced by a one cubic centimeters syringe at adaptor 470 through main needle 420. At the same time or shortly before or after, second component including a silk protein and optionally a least one cell type may be introduced with a one cubic centimeter syringe at adaptor 480. When the first and second components combine at the exit of delivery assembly 400 (at, e.g., an infarct region), the materials combine (mix, contact) to form a self-reinforcing composite matrix.

Figure 5A:
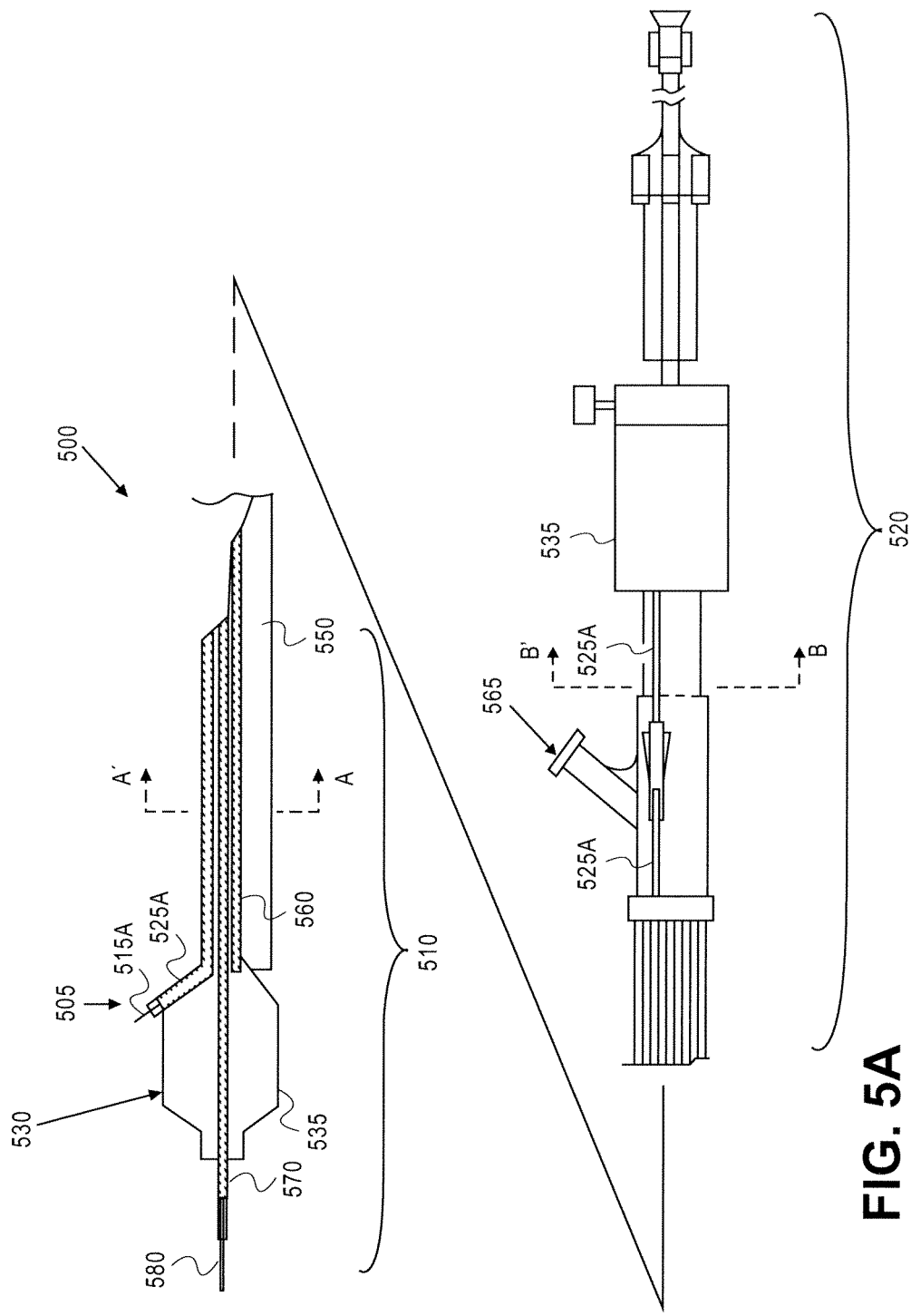
FIGS. 5A-5C illustrate a second alternative embodiment of a dual bore delivery device.
Figure 5B:
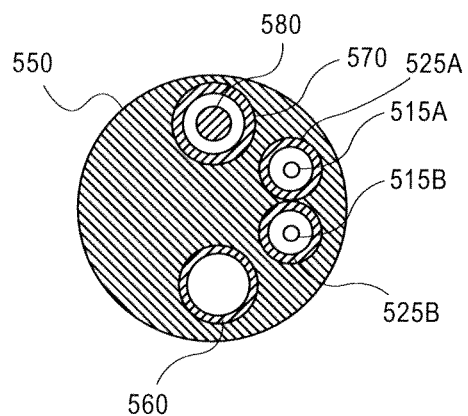
Figure 5C:
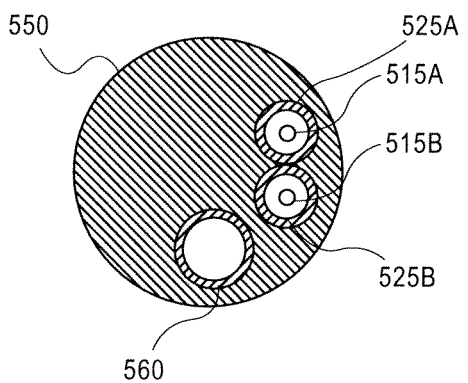

FIGS. 5A-5C illustrate an alternative embodiment of a dual-needle injection device which can be used to deliver two-component gel compositions of the present invention. In general, the catheter assembly 500 provides a system for delivering substances, such as two-component gel compositions, to or through a desired area of a blood vessel (a physiological lumen) or tissue in order to treat a myocardial infarct region or other treatment region. The catheter assembly 500 is similar to the catheter assembly 500 described in commonly-owned, U.S. Pat. No. 6,554,801, titled "Directional Needle Injection Drug Delivery Device", which is incorporated herein by reference.

In one embodiment, catheter assembly 500 is defined by elongated catheter body 550 having proximal portion 520 and distal portion 510. Guidewire cannula 570 is formed within catheter body (from proximal portion 510 to distal portion 520) for allowing catheter assembly 500 to be fed and maneuvered over guidewire 580. Balloon 530 is incorporated at distal portion 510 of catheter assembly 500 and is in fluid communication with inflation cannula 560 of catheter assembly 500.

Balloon 530 can be formed from balloon wall or membrane 535 which is selectively inflatable to dilate from a collapsed configuration to a desired and controlled expanded configuration. Balloon 530 can be selectively dilated (inflated) by supplying a fluid into inflation cannula 560 at a predetermined rate of pressure through inflation port 565 (located at proximal end 520). Balloon wall 535 is selectively deflatable, after inflation, to return to the collapsed configuration or a deflated profile. Balloon 530 may be dilated (inflated) by the introduction of a liquid into inflation cannula 560. Liquids containing treatment and/or diagnostic agents may also be used to inflate balloon 530. In one embodiment, balloon 530 may be made of a material that is permeable to such treatment and/or diagnostic liquids. To inflate balloon 530, the fluid can be supplied into inflation cannula 560 at a predetermined pressure, for example, between about one and 20 atmospheres. The specific pressure depends on various factors, such as the thickness of balloon wall 535, the material from which balloon wall 535 is made, the type of substance employed and the flow-rate that is desired.

Catheter assembly 500 also includes at least two substance delivery assemblies 505a and 505b (not shown; see FIGS. 5B-5C) for injecting a substance into a myocardial infarct region or other treatment region. In one embodiment, substance delivery assembly 505a includes needle 515a movably disposed within hollow delivery lumen 525a. Delivery assembly 505b includes needle 515b movably disposed within hollow delivery lumen 525b (not shown; see FIGS. 5B-5C). Delivery lumen 525a and delivery lumen 525b each extend between distal portion 510 and proximal portion 520. Delivery lumen 525a and delivery lumen 525b can be made from any suitable material, such as polymers and copolymers of polyamides, polyolefins, polyurethanes and the like. Access to the proximal end of delivery lumen 525a or delivery lumen 525b for insertion of needle 515a or 515b, respectively is provided through hub 535 (located at proximal end 520). Delivery lumens 525a and 525b may be used to deliver first and second components of a two-component gel composition to a post-myocardial infarct region.

FIG. 5B shows a cross-section of catheter assembly 500 through line A-A' of FIG. 5A (at distal portion 510). FIG. 5C shows a cross-section of catheter assembly 500 through line B-B' of FIG. 5A. In some embodiments, delivery assemblies 505a and 505b are adjacent to each other. The proximity of delivery assemblies 505a and 505b allows each component of the two-component gelation system to rapidly gel when delivered to a treatment site, such as a post-myocardial infarct region.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A composition comprising:
a first component of a two-component gelation system;
a second component of a two-component gelation system;
a block copolymer of silk protein conjugated with a glycosaminoglycan; and
at least one cell type, and
wherein the block copolymer of silk protein conjugated with a glycosaminoglycan and the at least one cell type are in an aqueous solution that form a self-reinforcing composite matrix in vivo when combined with the first component and the second component of the two-component gelation system.

2. The composition of claim 1, wherein the two-component gelation system is a fibrin glue system.

3. The composition of claim 2, wherein the two-component gelation system is a fibrin glue system comprising fibrinogen or a derivative thereof as the first component and thrombin as the second component.

4. The composition of claim 1, wherein the block copolymer of silk protein is synthetic.

5. The composition of claim 1 wherein at least one of the first component and the second component is in a solid phase.

6. The composition of claim 5, wherein the block copolymer of silk protein is up to 50 mass percent of the solid phase mixture.

7. The composition of claim 1, wherein the at least one cell type is in the form of a suspension comprising between 0.5 million to 10 million cells.

8. The composition of claim 1, wherein the at least one cell type is at least one of cardiomyocytes, chondrocytes or bone marrow mononuclear cells.

9. The composition of claim 1, wherein the at least one cell type is at least one of adipose tissue derived stem cells, embryonic stem cells, umbilical-cord-blood-derived stem cells, smooth muscle cells or skeletal myoblasts.

10. The composition of claim 1, wherein the first component and the second component is combined in a 1:1 ratio.

11. The composition of claim 1, wherein the block copolymer of silk protein is in an aqueous solution and combined with a growth factor.

12. The composition of claim 11, wherein the growth factor is selected from the group consisting of insulin-like growth factor 1, hepatocyte growth factor, vasoendothelial growth factor, beta-platelet derived growth factor, stem cell factor, granulocyte-colony stimulating factors, or platelet derived growth factor.

13. A kit comprising:
a first syringe comprising precursors of a two-component gelation system;
a second syringe comprising a block copolymer of silk protein conjugated with a glycosaminoglycan and at least one cell type in an aqueous solution; and
a third syringe comprising a first aqueous buffer solution in a pH range from about 7.5 to about 9.0.

14. The kit of claim 13, wherein the two-component gelation system is a fibrin glue system.

15. The kit of claim 14, wherein the two-component gelation system is a fibrin glue system comprising fibrinogen or a derivative thereof as the first component and thrombin as the second component.

16. The kit of claim 13, wherein the or block copolymer of silk protein is synthetic.

17. The kit of claim 13, wherein the block copolymer of silk protein comprises about one-tenth mass of the precursors.

18. The kit of claim 13, wherein the glycosaminoglycan is one of hyaluronic acid, heparin sulfate, chondroitin sulfate or keratin sulfate.

19. The composition of claim 1, wherein the glycosaminoglycan is one of hyaluronic acid, heparin sulfate, chondroitin sulfate or keratin sulfate.

20. The kit of claim 13, wherein the at least one cell type is in the form of a suspension comprising between 0.5 million to 10 million cells.

21. The kit of claim 13, wherein the at least one cell type is at least one of cardiomyocytes, chondrocytes or bone marrow mononuclear cells.

22. The kit of claim 13, wherein the at least one cell type is at least one of adipose tissue derived stem cells, embryonic stem cells, umbilical-cord-blood-derived stem cells, smooth muscle cells or skeletal myoblasts.

23. The composition of claim 11, wherein the growth factor is encapsulated, suspended, disposed within or loaded into a biodegradable microfiber or microparticle.

24. The kit of claim 13, wherein the aqueous solution within the second syringe further comprises a biologic encapsulated, suspended, disposed within or loaded into a biodegradable microfiber or microparticle.

* * * * *